United States Patent
Anderson et al.

(10) Patent No.: US 11,617,509 B2
(45) Date of Patent: Apr. 4, 2023

(54) OPHTHALMIC DEVICE

(71) Applicant: Optos PLC, Dunfermline (GB)

(72) Inventors: Alan Anderson, Dunfermline (GB); Iain Gourlay, Dunfermline (GB); Praveen Ashok, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 515 days.

(21) Appl. No.: 16/637,075

(22) PCT Filed: Aug. 14, 2017

(86) PCT No.: PCT/EP2017/070575
§ 371 (c)(1),
(2) Date: Feb. 6, 2020

(87) PCT Pub. No.: WO2019/034228
PCT Pub. Date: Feb. 21, 2019

(65) Prior Publication Data
US 2020/0237217 A1    Jul. 30, 2020

(51) Int. Cl.
*A61B 3/14*    (2006.01)
*A61B 3/10*    (2006.01)
(Continued)

(52) U.S. Cl.
CPC .......... *A61B 3/152* (2013.01); *A61B 3/0025* (2013.01); *A61B 3/0041* (2013.01);
(Continued)

(58) Field of Classification Search
CPC ..... A61B 3/152; A61B 3/0025; A61B 3/0041; A61B 3/0091; A61B 3/102; A61B 3/1025; A61B 3/1225
(Continued)

(56) References Cited

U.S. PATENT DOCUMENTS

| 5,596,339 A | 1/1997 | Furness, III et al. |
| 5,815,242 A | 9/1998 | Anderson et al. |

(Continued)

FOREIGN PATENT DOCUMENTS

| JP | 2012148003 A | 8/2012 |
| JP | 2013153793 A | 8/2013 |

(Continued)

OTHER PUBLICATIONS

English translation of Notice of Reasons for Refusal issued in Japanese Patent Office Application No. 2020-508467 dated Apr. 6, 2021.
(Continued)

*Primary Examiner* — Mahidere S Sahle
(74) *Attorney, Agent, or Firm* — DeLucia, Mlynar & Associates LLP

(57) ABSTRACT

An ophthalmic device including an illumination module which scans light across a region of the retina of an eye when the pupil is disposed at a focal point of the illumination module. The ophthalmic device further comprises components (2, 3-1, 4-1) for: aligning the pupil with the focal point; monitoring a position of the pupil relative to the focal point and maintaining the alignment based on the monitored position; aligning a scan location of the illumination module on the retina to a target scan location while the alignment of the pupil with the focal point is being maintained, wherein the illumination module performs a scan at the target scan location. The ophthalmic device further maintains the scan location at the target scan location while the alignment of the pupil with the focal point is being maintained, using scan location correction information based on retinal feature information.

20 Claims, 18 Drawing Sheets

(51) Int. Cl.
*A61B 3/15* (2006.01)
*A61B 3/00* (2006.01)
*A61B 3/12* (2006.01)

(52) U.S. Cl.
CPC ............ *A61B 3/0091* (2013.01); *A61B 3/102* (2013.01); *A61B 3/1025* (2013.01); *A61B 3/1225* (2013.01)

(58) Field of Classification Search
USPC ........................................ 351/205, 206, 221
See application file for complete search history.

(56) References Cited

U.S. PATENT DOCUMENTS

| | | | |
|---|---|---|---|
| 7,637,615 B2* | 12/2009 | Yamada | A61B 3/113 351/205 |
| 7,703,922 B2* | 4/2010 | Van de Velde | A61B 3/1025 351/221 |
| 8,970,847 B2 | 3/2015 | Ono | |
| 2008/0100612 A1 | 5/2008 | Dastmalchi et al. | |
| 2012/0189184 A1 | 7/2012 | Matsumoto et al. | |
| 2012/0274897 A1 | 11/2012 | Scott | |
| 2013/0195336 A1 | 8/2013 | Uchida | |
| 2013/0229623 A1 | 9/2013 | Murase | |
| 2014/0300864 A1 | 10/2014 | Fukuma | |
| 2014/0320810 A1 | 10/2014 | Fukuma | |
| 2015/0282707 A1 | 10/2015 | Tanabe et al. | |
| 2016/0089024 A1 | 3/2016 | Katashiba | |
| 2016/0360959 A1 | 12/2016 | Heeren et al. | |
| 2017/0251918 A1* | 9/2017 | Plaian | G02B 5/005 |
| 2017/0325679 A1 | 11/2017 | Ishiai et al. | |

FOREIGN PATENT DOCUMENTS

| | | |
|---|---|---|
| JP | 2013-180126 A | 9/2013 |
| JP | 2014-512239 A | 5/2014 |
| JP | 2014-200680 A | 10/2014 |
| JP | 2016 97181 A | 5/2016 |
| JP | 2016067551 A | 5/2016 |
| JP | 2016097181 A | 5/2016 |
| JP | 2016106962 A | 6/2016 |
| JP | 2016140360 A | 8/2016 |
| JP | 3 150 109 A1 | 4/2017 |
| JP | 2017-064407 A | 4/2017 |
| JP | 2017-64407 A | 4/2017 |
| JP | 2017 124204 A | 7/2017 |
| WO | WO95/13012 A2 | 5/1995 |
| WO | WO2008/009877 A1 | 1/2008 |
| WO | WO2018/069345 A1 | 4/2018 |
| WO | WO2018/069346 A1 | 4/2018 |

OTHER PUBLICATIONS

Notice of Reasons for Refusal issued in Japanese Patent Office Application No. 2020-508467 dated Apr. 6, 2021 (Japanese Version with English Machine Translation attached).
Office Action issued by the China National Intellectual Property Administration on corresponding China patent application No. 2017800955565 dated Dec. 28, 2021 (14 sheets) (Machine English Summary/Translation attached; 11 pages).
International Search Report issued in international application No. PCT/EP2017/070575.
Written opinion of the International Searching Authority issued in international application No. PCT/EP2017/070575.
U.S. Appl. No. 16/636,999, filed Feb. 6, 2020.
U.S. Appl. No. 16/637,023, filed Feb. 6, 2020.
U.S. Appl. No. 16/637,052, filed Feb. 6, 2020.
Notice of Reasons for Refusal (dated Oct. 6, 2021 and) issued in Japanese Patent Application 2020-508467 (10 sheets); English translation attached (14 sheets).
Decision of Refusal dated May 17, 2022 in Japanese Patent Application 2020-508467 (10 sheets); English translation attached (14 sheets).

* cited by examiner

OPHTHALMIC DEVICE

This application is a national phase filing under 37 U.S.C. § 371 based on International Application No. PCT/EP2017/070575, filed Aug. 14, 2017, and claims the benefit of priority of that International Application. The contents of the International Application are incorporated by reference herein.

TECHNICAL FIELD

The present invention generally relates to the field of ophthalmic devices and, more particularly, to ophthalmic devices having an illumination module for scanning light across a region of the retina of a subject's eye.

BACKGROUND

Some ophthalmic devices for imaging the retina of an eye or treating the eye with light of appropriate wavelength and intensity employ wide field-of-view (FOV) optics that allow almost any portion of the retina to be illuminated or imaged, without needing to enlarge the pupil or alter the patient's gaze direction. Such wide FOV optics may enable the patient to adopt a more comfortable and natural central gaze that is easy to maintain, thereby reducing or avoiding problems case by gaze fixation errors. An example of such ophthalmic device is described in U.S. Pat. No. 5,815,242.

SUMMARY

With a smaller pupil size, however, the optical scanning beam passing through the pupil is more prone to being 'clipped' by the edge of the pupil as the pupil moves relative to the focal point of the ophthalmic device owing to involuntary movements of the patent's eye that occur during the scan. In addition, small variations in the patient's gaze direction can make it difficult to maintain the scan location of the ophthalmic device on the retina at a target location. Thus, both the pupil position and gaze direction need to be more precisely held or their changes effectively compensated for in order to achieve a successful scan, particularly in cases where the scan takes a long time to complete, such an optical coherence tomography (OCT) scan.

With these points in mind, the inventors have devised a method of operating an ophthalmic device having an illumination module arranged to scan light across a region of the retina of a subject's eye to illuminate said region. The method comprises aligning the pupil of the eye with a focal point of the illumination module and, following the alignment of the pupil with the focal point, monitoring a position of the pupil relative to the focal point and maintaining the alignment of the pupil with the focal point based on the monitored position. The method further comprises performing, while the alignment of the pupil with the focal point is being maintained based on the monitored position, processes of: aligning a scan location of the illumination module on the retina to a target scan location; and maintaining the scan location at the target scan location, by: acquiring retinal feature information from a monitored portion of the retina; processing the acquired retinal feature information to generate scan location correction information; and maintaining the scan location at the target scan location using the generated scan location correction information. The method further comprises performing a scan at the target scan location to illuminate a region of the retina at the target scan location while the scan location is being maintained at the target scan location using the generated scan location correction information.

The inventors have further devised an ophthalmic device comprising an illumination module arranged to scan light across a region of the retina of a subject's eye to illuminate said region when the pupil of the eye is disposed at a focal point of the illumination module. The illumination module comprises: a reflecting face arranged to reflect light emitted by an emission section and to scan the light in a specific direction by changing orientation; and a concave mirror face arranged to reflect the light that has been reflected by the reflecting face onto the retina of the subject's eye when the subject's eye is placed at a focal point of the concave mirror during use of the ophthalmic device. The ophthalmic device further comprises a pupil alignment module arranged to align the pupil of the eye with the focal point, and a pupil alignment maintenance module arranged to, following the alignment of the pupil with the focal point by the pupil alignment module, monitor a position of the pupil relative to the focal point and maintain the alignment of the pupil with the focal point based on the monitored position. The ophthalmic device further comprises a retina scan location alignment module arranged to align a scan location of the illumination module on the retina to a target scan location while the alignment of the pupil with the focal point is being maintained by the pupil alignment maintenance module, wherein the illumination module is arranged to perform a scan at the target scan location to illuminate a region of the retina at the target scan location. The ophthalmic device further comprises a retina scan location maintenance module arranged to maintain the scan location at the target scan location by performing, while the alignment of the pupil with the focal point is being maintained by the pupil alignment maintenance module, processes of: acquiring retinal feature information from a monitored portion of the retina; processing the acquired retinal feature information to generate scan location correction information; and maintaining the scan location at the target scan location using the generated scan location correction information.

BRIEF DESCRIPTION OF THE DRAWINGS

Embodiments of the invention will now be explained in detail, by way of example only, with reference to the accompanying figures, in which.

DETAILED DESCRIPTION OF EMBODIMENTS

Embodiments of the present invention will now be described in detail with reference to the accompanying drawings.

Embodiment 1

Figure 1:
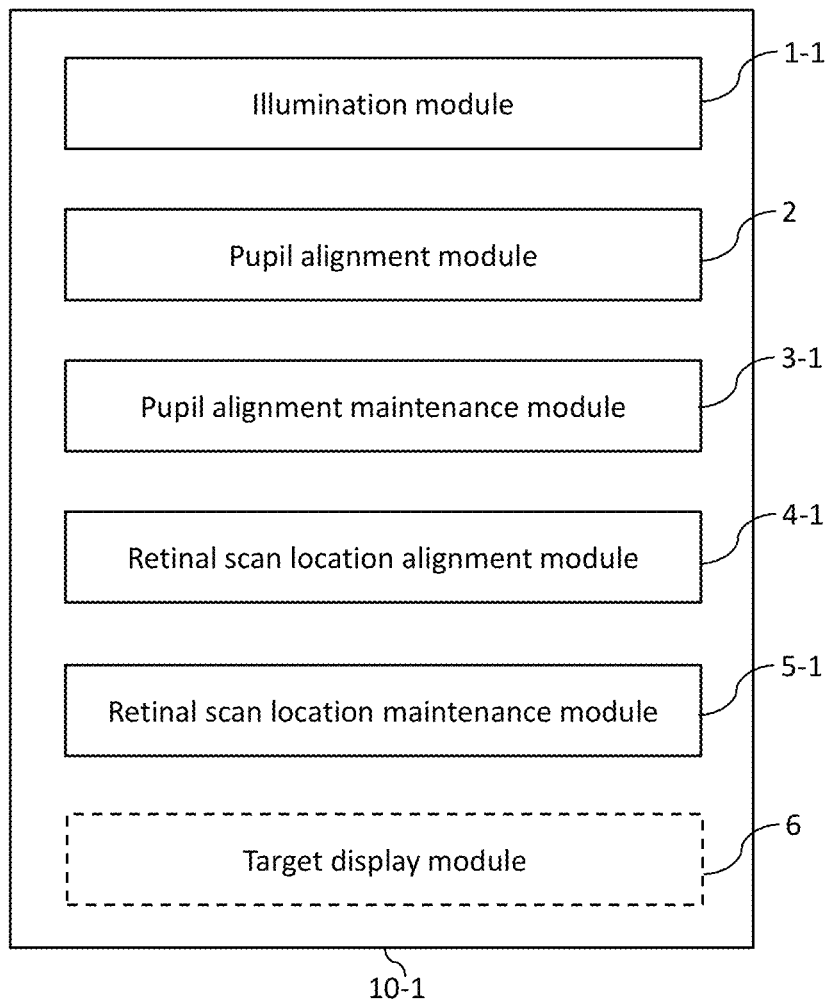
FIG. 1 is a schematic illustration of an ophthalmic device according to a first embodiment of the present invention.

FIG. 1 is a schematic illustration of an ophthalmic device 10-1 according to a first embodiment of the invention, which comprises an illumination module 1-1 that is operable to scan light across a region of the retina of a subject's eye (not shown in FIG. 1) to illuminate said region when the pupil of the eye is placed at a focal point of the illumination module 1-1. The illumination module 1-1 comprises a reflecting face arranged to reflect scanning light emitted by an emission section and to scan the scanning light in a specific direction by changing orientation, and a concave mirror face arranged to reflect the scanning light that has been reflected by the reflecting face onto the retina of the subject's eye when the subject's eye is placed at a focal point of the concave mirror during use of the ophthalmic device 10-1. The scanning light from the emission section, which travels via the reflecting face and the concave mirror face, pivots about focal point as the scan is being performed. The emission section may comprise a laser configured to emit a light beam whose characteristics (such as wavelength and intensity) are suitable for treating the retina, for example. Exemplary configurations of the illumination module 1-1 are described in more detail below.

The ophthalmic device 10-1 further comprises a pupil alignment module 2, a pupil alignment maintenance module 3-1, a retina scan location alignment module 4-1, and a retina scan location maintenance module 5-1, the details of which are also described in more detail below.

The ophthalmic device 10-1 may, as in the present embodiment, further comprise a target display module 6, which is arranged to display to the subject a fixation target for setting the gaze direction of the subject's eye, preferably in a central gaze direction such that the subject looks 'straight ahead', in order to reduce or avoid eye strain, and avoid fixation errors and involuntary eye movements that typically occur when eye-steering is employed and the subject is consequently required to adopt a non-central gaze direction.

The target display module 6 may be operable in a static fixation mode to display the fixation target using a patient alignment module (PAM) or the like, and in a dynamic fixation mode to display the fixation target emitted from one or more fixation target light sources via the concave mirror face while a scan of the retina is being performed. The target display module 6 may thus display the fixation target to the subject throughout the sequence of operations that is performed by the pupil alignment module 2, the pupil alignment maintenance module 3-1, the retina scan location alignment module 4-1 and the retina scan location maintenance module 5-1 described herein, in order to fix the subject's gaze and keep it fixed, preferably in the central gaze direction.

Exemplary arrangements of one or more fixation target light sources and optionally other components in an ophthalmic device, as well as control arrangements for controlling their operation, which can together provide the functionality of the target display module 6 (when it operates in the dynamic fixation mode) in displaying a fixation target to the subject during the performance of a retinal scan, are described in the applicant's co-pending application titled "Ophthalmic Device", which was filed on the same date as the present application with agent reference number 198 409, the contents of which are incorporated herein by reference in their entirety. In brief, the ophthalmic device described in that application comprises at least one light source arranged to emit a fixation target light, as well as a reflecting face and a concave mirror face as set out above, and is arranged such that, when the subject's eye is placed at the focal point of the concave mirror during use of the ophthalmic device and when the light source emits the fixation target light, the fixation target light and the scanning light are simultaneously incident on the ocular fundus of the subject's eye via different optical paths both propagating via the concave mirror face and the focal point, the target fixation light following a predetermined optical path for fixing the gaze of the subject's eye. Several embodiments of such an ophthalmic device are summarised on pages 1-5 and subsequently described in more detail with reference to the drawings in the applicant's co-pending application titled "Ophthalmic Device", which was filed on the same date as the present application with agent reference number 198 409. At least some of the features of one or more of these embodiments may be claimed in the present application.

In the following, an overview of the functionality of the pupil alignment module 2, the pupil alignment maintenance module 3-1, the retina scan location alignment module 4-1, and the retina scan location maintenance module 5-1 is provided, followed by a more detailed description of another exemplary implementation of the ophthalmic device and its operation according to a second embodiment.

The pupil alignment module 2 is arranged to align the pupil of the eye with the focal point of the illumination module 1-1 (specifically, a focal point of the concave mirror face of the illumination module 1-1). The pupil alignment module 2 may, as in the present embodiment, be arranged to align the pupil of the eye with the focal point by monitoring the position of the pupil relative to the focal point and, based on the monitored position, automatically adjusting the focal point of the illumination module 1-1 so as to bring the focal point into alignment with the pupil. The focal point may be adjusted by controlling a stepper motor or other moving mechanism to move the illumination module 1-1 relative to the eye, and additionally or alternatively changing the configuration of optical components within the illumination module 1-1 using techniques known to those skilled in the art in order to adjust the focal point so as to bring it into alignment with the pupil of the eye.

The pupil alignment module 2 may alternatively be arranged to align the pupil of the eye with the focal point by monitoring the position of the pupil relative to the focal point and generating, based on the monitored position, signals (for example, visual signals, audio signals and/or tactile feedback signals e.g. in the form of a vibrating grip, footplate or other device that is in contact with the subject) to guide the subject in moving their eye so that the pupil of the eye is brought into alignment with the focal point. The pupil alignment module 2 may additionally or alternatively generate, based on the monitored position, signals of the aforementioned kind(s) to guide an ophthalmologist or the like who is overseeing the operation of the ophthalmic device 10-1 to control the focal point of the illumination module 1-1, via any appropriate user interface (e.g. keyboard and mouse) connected to the illumination module 2, so as to bring the focal point of the illumination module 1-1 into alignment with the pupil.

The pupil alignment maintenance module 3-1 is arranged to, following the alignment of the pupil with the focal point by the pupil alignment module 2, monitor the position of the pupil relative to the focal point of the illumination module 1-1 and maintain the alignment of the pupil with the focal point based on the monitored position. The pupil alignment maintenance module 3-1 may, as in the present embodiment, be arranged to maintain the alignment of the pupil with the focal point by monitoring the position of the pupil relative to the focal point and, based on the monitored position, automatically adjusting the focal point of the illumination module 1-1 so as to maintain the alignment. The focal point may be adjusted by moving the illumination module 2 relative to the eye, and additionally or alternatively changing the configuration of optical components within the illumination module 1-1, as noted above.

The pupil alignment maintenance module 3-1 may alternatively be arranged to maintain the alignment of the pupil with the focal point by monitoring the position of the pupil relative to the focal point and generating, based on the monitored position, signal(s) of the kind(s) mentioned above to guide the subject in moving their eye so that the pupil of the eye is kept in alignment with the focal point. The pupil alignment module 2 may additionally or alternatively generate, based on the monitored position, signal(s) of the aforementioned kind(s) to guide an ophthalmologist or the like who is overseeing the operation of the ophthalmic device 10-1 to control the focal point of the illumination module 1-1 so as to keep the focal point of the illumination module 1-1 in alignment with the pupil.

The retina scan location alignment module 4-1 is arranged to align a scan location of the illumination module 1-1 on the retina to a target scan location while the alignment of the pupil with the focal point of the illumination module 1-1 is being maintained by the pupil alignment maintenance module 3-1. The illumination module 1-1 is arranged to subsequently perform a scan at the target scan location to illuminate a region of the retina at the target scan location.

The retina scan location alignment module 4-1 may, as in the present embodiment, align the scan location of the illumination module 1-1 on the retina to the target scan location by determining an offset indicator that is indicative of an offset between a designated scan location on the retina and an initial scan location of a scan performed by the illumination module 1-1. The offset indicator may be determined in any suitable or desirable way, and an exemplary method of determining the offset indicator is described below. The retina scan location alignment module 4-1 may then control the illumination module 1-1, based on the determined offset indicator, to move the scan location of the illumination module 1-1 from the initial scan location to a destination scan location that is closer to the designated scan location than is the initial scan location, the destination scan location being the target scan location. Alternatively, in embodiments where the imaging axis (that is central to the field-of-view) of the illumination module 1-1 cannot be rotated about the focal point, the retina scan location alignment module 4-1 may be arranged to align the scan location of the illumination module 1-1 on the retina to the target scan location by controlling the target display module 6, based on the determined offset indicator, to display the target so as to set the gaze of the subject's eye in a gaze direction which brings the scan location of the illumination module 1-1 into alignment with the target scan location.

The retina scan location maintenance module 5-1 is arranged to maintain the scan location at the target scan location by performing, while the alignment of the pupil with the focal point is being maintained by the pupil alignment maintenance module 3-1, processes of: (i) acquiring retinal feature information from a monitored portion of the retina; (ii) processing the acquired retinal feature information to generate scan location correction information; and (iii) maintaining the scan location at the target scan location using the generated scan location correction information.

The retina scan location maintenance module 5-1 may, as in the present embodiment, be arranged to maintain the scan location at the target location by: acquiring, as the retinal feature information, images of the monitored portion of the retina while the scan is being performed by the illumination module 1-1; generating, as the scan location correction information, indications of respective offsets between a designated scan location and scan locations of the acquired images of the retina; and controlling the illumination module 1-1, based on the scan location correction information, to maintain the scan location at the target scan location. Alternatively, in embodiments where the imaging axis of the illumination module 1-1 cannot be rotated about the focal point, the retina scan location maintenance module 5-1 may be arranged to maintain the scan location at the target location by: acquiring, as the retinal feature information, images of the monitored portion of the retina while the scan is being performed by the illumination module 1-1; generating, as the scan location correction information, indications of respective offsets between a designated scan location and scan locations of the acquired images on the retina; and controlling the target display module 6, based on the scan location correction information, to vary a characteristic of the displayed target (for example, its colour) so as to maintain the gaze direction of the subject's eye and keep the scan location at the target scan location. Exemplary implementations of the retina scan location maintenance module 5-1 are described in more detail below.

Figure 2:
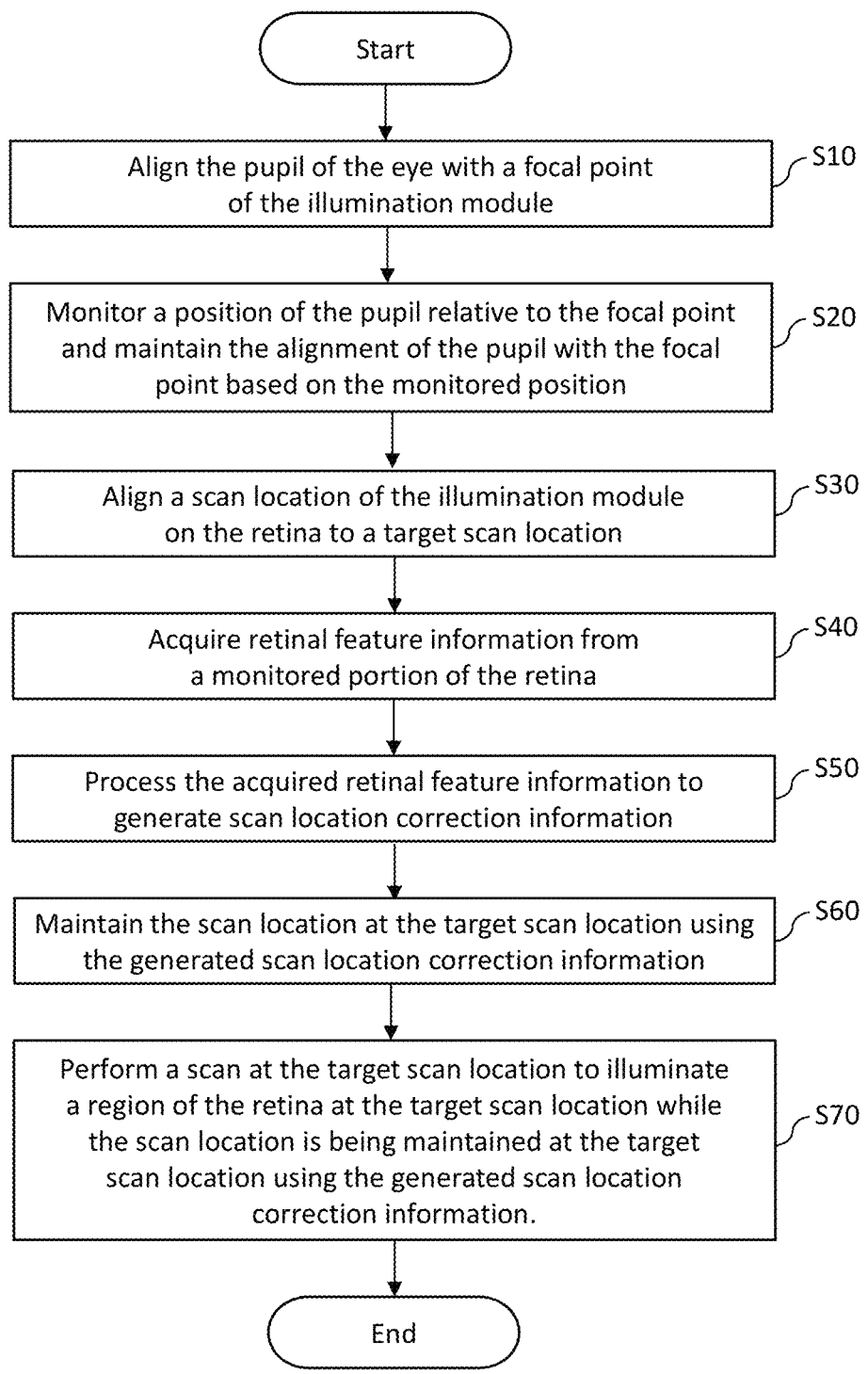
FIG. 2 is a flow diagram illustrating a method of operating the ophthalmic device of the first embodiment.

FIG. 2 is a flow chart illustrating a method of operating the ophthalmic device 10-1 shown in FIG. 1 to perform a scan at a target scan location on the retina so as to illuminate a region of the retina at the target scan location.

In process S10, the pupil alignment module 2 aligns the pupil of the eye with the focal point of the illumination module 1-1. During this process, the target display module 6 may, as in the present embodiment, operate in the static fixation mode to display a fixation target for fixing the gaze of the subject's eye 38 in a central gaze direction. In process S10, pupil alignment may be achieved using techniques known to those skilled in the art, for example with the use of a patient alignment module (PAM) having a stereoscopic camera that is configured to determine the pupil position from acquired images of eye. The pupil position thus monitored by the pupil alignment module 2 may be compared with the position of the focal point of the illumination module 1-1 to determine a correction that is required to bring the pupil into alignment with the focal point. As noted above, the pupil alignment module 2 of the present embodiment automatically adjusts the position of the focal point of the illumination module 1-1 (in the x, y and z directions) so as to bring the focal point into alignment with the pupil using the determined correction, although it may alternatively generate, based on the correction, signal(s) of the aforementioned kind(s) to guide the subject in moving their eye so that the pupil of the eye is brought into alignment with the focal point. For example, the pupil alignment module 2 may control the target display module 6 to vary a characteristic of the displayed fixation target (e.g. its colour) in order to provide the subject with feedback regarding the current degree of alignment of the pupil with the focal point. The pupil alignment module 2 may additionally or alternatively generate, based on the monitored position, signal(s) of the aforementioned kind(s) that are indicative of the required correction in order to guide an ophthalmologist or the like who is overseeing the operation of the ophthalmic device 10-1 to control the focal point of the illumination module 1-1 so as to bring the focal point of the illumination module 1-1 into alignment with the pupil.

Following the alignment of the pupil with the focal point, the ophthalmic device 10-1 starts a procedure for performing a scan of a part of the retina, and the target display module 6 switches from operating in the static fixation mode to operating in the dynamic fixation mode.

In process S20, the pupil alignment maintenance module 3-1 monitors the position of the pupil relative to the focal point and actively maintains the alignment of the pupil with the focal point based on the monitored position. The monitored pupil position may be compared with the position of the focal point of the illumination module 1-1 to determine a correction that is required to maintain the alignment of the pupil with the focal point. As noted above, the pupil alignment maintenance module 3-1 of the present embodiment uses the determined correction to automatically adjust the position of the focal point of the illumination module 1-1 (in the x, y and z directions) so as to maintain the alignment of the focal point with the pupil (in other words, to use a closed-loop control system to at least partially compensate for pupil movement), or it may alternatively generate, based on the correction, signal(s) of the above-mentioned kind(s) to guide the subject in moving their eye so as to maintain the alignment of the pupil with the focal point. For example, the pupil alignment maintenance module 3-1 may control the target display module 6 to vary a characteristic of the displayed fixation target (e.g. its colour) in order to provide the subject with feedback regarding the current degree of alignment of the pupil with the focal point. The pupil alignment maintenance module 3-1 may additionally or alternatively generate, based on the monitored position, signal(s) of the aforementioned kind(s) that are indicative of the required correction; these signals (e.g. audio and/or visual signals, which may be conveyed via any suitable user interface (UI) known to those skilled in the art, such as that of a conventional personal computer) may be used to guide an ophthalmologist or the like who is overseeing the operation of the ophthalmic device 10-1 to control the focal point of the illumination module 1-1 so as to maintain the alignment of the focal point of the illumination module 1-1 with the pupil.

In process S30, while the alignment of the pupil with the focal point is being maintained by the pupil alignment maintenance module 3-1 on the basis of the monitored position, the retinal scan location alignment module 4-1 aligns a scan location of the illumination module 1-1 on the retina to a target scan location. In the present embodiment, the retinal scan location alignment module 4-1 aligns a scan location of the illumination module 1-1 on the retina to a target scan location by determining the aforementioned offset indicator, and controlling the illumination module 1-1, based on the determined offset indicator, to move the scan location of the illumination module 1-1 from the initial scan location to a destination scan location that is closer to the designated scan location than is the initial scan location, the destination scan location being the target scan location. Alternatively, the retinal scan location alignment module 4-1 may align a scan location of the illumination module 1-1 on the retina to a target scan location by determining the aforementioned offset indicator, and controlling the target display module 6, based on the determined offset indicator, to display the target so as to set the gaze of the subject's eye in a gaze direction which brings the scan location of the illumination module 1-1 into alignment with the target scan location. The retinal scan location alignment module 4-1 may further control the target display module 6 to vary a characteristic of the displayed fixation target (e.g. its colour) in order to provide the subject with feedback regarding the current degree of alignment of the scan location of the illumination module 1-1 on the retina to the target scan location.

The retina scan location maintenance module 5-1 then maintains the scan location at the target scan location by performing processes S40 to S60.

In process S40, the retina scan location maintenance module 5-1 acquires retinal feature information from a monitored portion of the retina. The retina scan location maintenance module 5-1 may, as in the present embodiment, acquire, as the retinal feature information, images of the monitored portion of the retina while the scan is being performed by the illumination module 1-1.

In process S50, the retina scan location maintenance module 5-1 processes the acquired retinal feature information to generate scan location correction information. The retina scan location maintenance module 5-1 may, as in the present embodiment, generate, as the scan location correction information, indications of respective offsets between a designated scan location and scan locations of the acquired images on the retina.

In process S60, the retina scan location maintenance module 5-1 maintains the scan location at the target scan location using the generated scan location correction information. The retina scan location maintenance module 5-1 may, as in the present embodiment, control the illumination module 1-1, based on the scan location correction information, to maintain the scan location at the target scan location. The retina scan location maintenance module 5-1 may alternatively control the target display module 6, based on the scan location correction information, to vary a characteristic of the displayed target (e.g. its colour) so as to maintain the gaze direction of the subject's eye and keep the scan location at the target scan location.

In process S70, while the scan location is being maintained at the target scan location by the using the generated scan location correction information, the illumination module 1-1 performs a scan at the target scan location to illuminate a region of the retina at the target scan location.

Through the performance of processes S10 to S70, the ophthalmic device 10-1 is able to reliably illuminate the targeted region of the retina over a prolonged period of time, whilst maintaining patient comfort.

Embodiment 2

Figure 3:
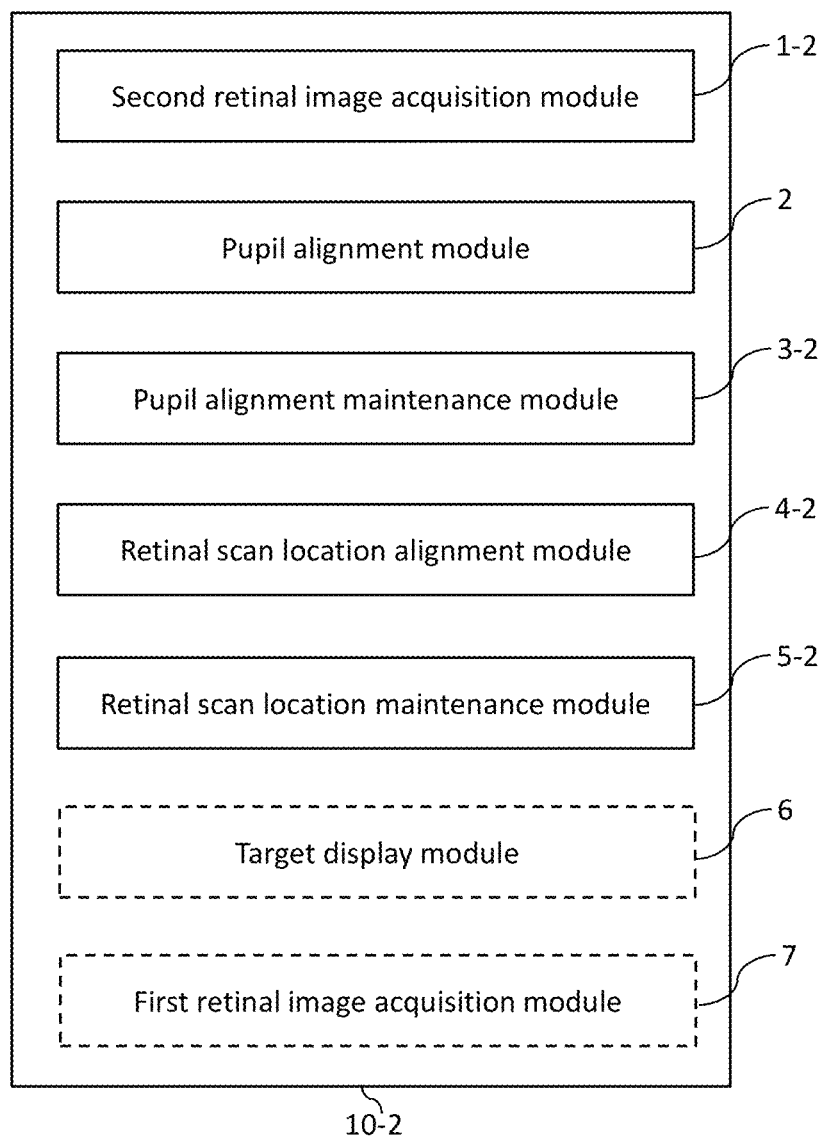
FIG. 3 is a schematic illustration of an ophthalmic device according to a second embodiment of the present invention.

An ophthalmic device 10-2 according to a second embodiment of the invention is illustrated in FIG. 3, where like components are labeled by the same numerals. The ophthalmic device 10-2 differs from ophthalmic device 10-1 by the configuration of the pupil alignment maintenance module 3-2, the retinal scan location alignment module 4-2, and the retinal scan location maintenance module 5-1, and by further comprising an imaging module in the exemplary form of a first retinal image acquisition module 7, which is arranged to scan light across a second region of the retina of the subject's eye, via the focal point, and receive light reflected from the second region when the eye is disposed at the focal point.

In this embodiment, the illumination module takes the exemplary form of a second retinal image acquisition module 1-2, which is configured to not only illuminate a region of the retina but also receive and process light reflected from the illuminated region so as to acquire an image of the region. The second retinal image acquisition module 1-2 is different from the first retinal image acquisition module 7, and may have a retinal image acquisition time that is longer than that of the first retinal image acquisition module 7. The second retinal image acquisition module 1-2 may be an OCT imaging device (as described in more detail below), or alternatively a high-density scanning laser ophthalmoscope (SLO) or a high-density confocal SLO, for example.

The first and second retinal image acquisition modules 7 and 1-2 may, as in the embodiment of FIG. 3, be operable in a combined imaging mode to transmit and receive light along a common optical path so as to concurrently image substantially the same region of the retina. The first and second retinal image acquisition modules 7 and 1-2 may, however, be operable in the combined imaging mode to transmit and receive light along respective optical paths having a fixed positional relationship to one another, so as to concurrently image respective regions of the retina that are different from one another. The second retinal image acquisition module 1-2 may thus be operable in the combined imaging mode to acquire a retinal image of an imaging region of the retina (which is provided at a scan location of the second retinal image acquisition module 1-2) having a predetermined positional relationship to the concurrently imaged imaging region of the first retinal image acquisition module 7 (which is provided at a scan location of the first retinal image acquisition module 7) for the eye under examination, and which need not be the same in size as the concurrently imaged imaging region of the first retinal image acquisition module 7. In other words, the respective imaging regions on the retina concurrently imaged by the first and second retinal image acquisition modules 7 and 1-2 may have centers (e.g. geometric centers) that are not coincident but offset from each other by a known amount in a known direction, which can be determined by calibration, for example.

Figure 4:
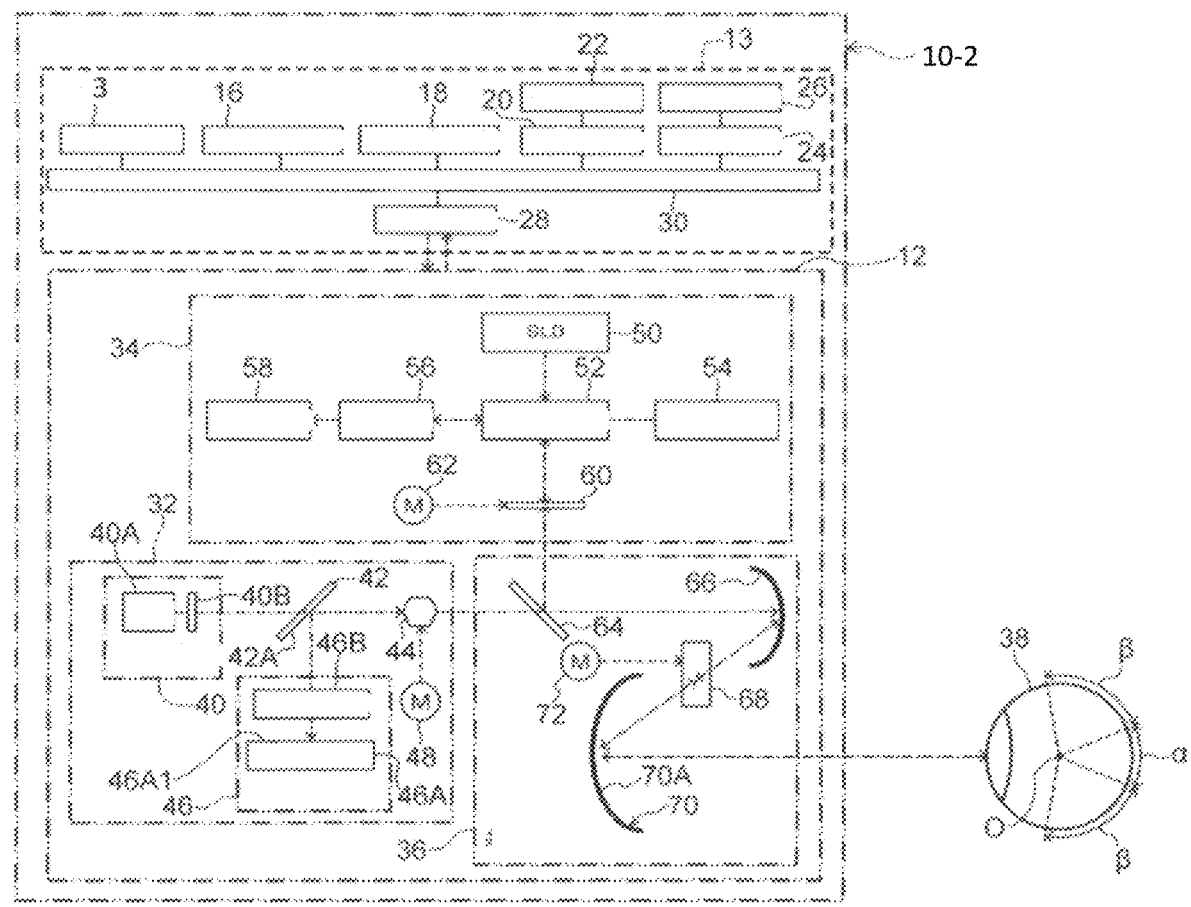
FIG. 4 is a block diagram illustrating an implementation of the ophthalmic device illustrated in FIG. 3, in the exemplary form of a combined SLO-OCT scanner.

The ophthalmic device 10-2 may, as illustrated in the embodiment of FIG. 4, take the exemplary form of a combined SLO and OCT scanner, comprising a device main body 12 that includes an SLO unit 32, an OCT unit 34, and a shared optical system 36. The ophthalmic device 10-2 also has a device main body controller 13 comprising a controller 3 which implements the functionality of the pupil alignment module 2, the pupil alignment maintenance module 3-2, the retina scan location alignment module 4-2, and the retina scan location maintenance module 5-2.

The ophthalmic device 10-2 thus includes SLO imaging system functionality, which is functionality for imaging using SLO, and OCT imaging system functionality, which is functionality for imaging using OCT. The SLO imaging system functionality is implemented by the device main body controller 13, the SLO unit 32, and the shared optical system 36. The OCT imaging system functionality is implemented by the device main body controller 13, the OCT unit 34, and the shared optical system 36. The SLO unit 32, the shared optical system 36 and the SLO image generator 18 shown in FIG. 4 together provide an example of the first retinal image acquisition module 7 of FIG. 3, and the OCT unit 34, the shared optical system 36 and the OCT image generator 16 together provide an example of the second retinal image acquisition module 1-2. Thus, the first and second retinal imaging modules 7 and 1-2 share some optical components (namely, the shared optical system 36) in the present embodiment. The first and second retinal imaging modules 7 and 1-2 may, however, alternatively be provided as separate units that do not share any optical components.

The ophthalmic device 10-2 is operable in an SLO mode, which is an operation mode that exercises the SLO imaging system functionality, an OCT mode, which is an operation mode that exercises the OCT imaging system functionality, and the aforementioned combined imaging mode that exercises both the SLO imaging system functionality and the OCT imaging system functionality at the same time. These operation modes may be selectively set according to user instructions or sequence control.

The SLO unit 32 may, as in the present embodiment, include an emission section 40, a beam splitter 42, a polygon mirror 44, a photo detector section 46, and a motor 48, that are configured to generate a two-dimensional image of the retina of a subject's eye 38.

Hereafter, in a case in which, for example, the ophthalmic device 10-2 is installed on a horizontal surface, a direction substantially perpendicular to the horizontal surface (not illustrated in the drawings) is denoted the "Y direction" for convenience of explanation. For example, a direction that is substantially parallel to a horizontal surface and that is the depth direction of the subject's eye 38 positioned in a state in which the anterior segment is facing an eyepiece lens (not illustrated in the drawings) of the ophthalmic device 10-2, in a case in which the ophthalmic device 10-2 is installed on the horizontal surface, is denoted the "Z direction" hereafter for convenience of explanation. Hereafter, a direction substantially perpendicular to both the Y direction and the Z direction is denoted the "X direction" hereafter for convenience of explanation.

The emission section 40 includes a light source 40A and a bandpass filter 40B. The light source 40A is a light source for imaging using SLO, and may emit light having a wavelength in a range of from approximately 400 nanometers to approximately 1100 nanometers. Light emitted from the light source 40A passes through the bandpass filter 40B such that only light having specific wavelengths is emitted onto the beam splitter 42.

In the present embodiment, light emitted from the emission section 40 is broadly split into visible red and green (RG) light and near-infrared light, which is light having a wavelength in the near-infrared region of the spectrum.

In the present embodiment, RG light and near-infrared light are selectively emitted from the emission section 40 by varying the wavelength of the light produced by the light source 40A, and by applying the bandpass filter 40B to the light produced by the light source 40A.

For convenience of explanation, RG light and near-infrared light, serving as the light emitted from the emission section 40, are simply referred to as "SLO light" hereafter in a case in which explanation does not need to distinguish between the two.

The beam splitter 42 guides the SLO light to the polygon mirror 44 by transmitting the SLO light, and guides first retina reflected light to the photo detector section 46. Here, first retina reflected light denotes light reflected by the retina originating from the SLO light. Light reflected by the retina denotes light that was reflected by the retina and was then incident on the shared optical system 36.

The polygon mirror 44 sends the SLO light from the beam splitter 42 to the shared optical system 36. Then, as illustrated as an example in FIG. 5, the polygon mirror 44 scans the SLO light in the Y direction by rotating in the arrow A direction on receiving drive force of the motor 48.

The photo detector section 46 includes a photo detector 46A and an optical filter 46B. The optical filter 46B is disposed at a position between an optical reception face 46A1 of the photo detector 46A and a reflecting face 42A of the beam splitter 42, and covers an optical reception face 46A1. First retina reflected light made of near-infrared light and first retina reflected light made of RG light are selectively made incident to the optical reception face 46A1.

The photo detector 46A generates an SLO image signal, which is an image signal based on the first retina reflected light that was incident via the optical filter 46B, and outputs the generated SLO image signal.

The OCT unit 34 is employed to generate a tomographic image of the retina, and may, as in the present embodiment, include a super-luminescent diode (SLD) 50, an optical coupler 52, a reference light optical system 54, a spectrophotometer 56, a line sensor 58, a V-galvanometer mirror 60, and a motor 62.

The SLD 50 emits low-coherence light. Low-coherence light, for example, denotes light encompassing light in the near-infrared region having a longer wavelength than near-infrared light emitted from the emission section 40 and having a time-wise coherence length of approximately several tens of micrometers.

Low-coherence light emitted from the SLD 50 is fed into the optical coupler 52 via a first optical fiber (not illustrated in the drawings) and is split into reference light and signal light. The reference light is guided to the reference light optical system 54 via a second optical fiber (not illustrated in the drawings), and the signal light is guided to the V-galvanometer mirror 60 via a third optical fiber (not illustrated in the drawings).

The reference light optical system 54 is an optical delay line which matches the optical path length between the eye 38 and the optical coupler 52.

A reference mirror returns reference light to the optical coupler 52 via the same optical path by reflecting the reference light. The reference mirror is a movable mirror that can move in the direction of the optical axis of the reference light, and the length of the optical path of the reference light is adjusted by moving the position of the reference mirror on the optical axis.

The V-galvanometer mirror 60 sends signal light to the shared optical system 36. Then, as illustrated as an example in FIG. 5, the V-galvanometer mirror 60 scans the signal light in the Y direction by rotationally oscillating in the arrow B direction on receiving drive force of the motor 62.

Moreover, the V-galvanometer mirror 60 guides second retina reflected light to the optical coupler 52 via a fourth optical fiber. Here, the second retina reflected light denotes light reflected by the retina originating from signal light.

The second retina reflected light guided by the optical coupler 52 is superimposed with the reference light guided from the reference light optical system to the optical coupler 52 by the optical coupler 52 and interference occurs. Interference light obtained due to the interference occurring is spectrally dispersed by the spectrophotometer 56, and the spectrally dispersed interference light is guided to the line sensor 58.

The line sensor 58 generates an OCT image signal, which is an image signal based on incident interference light, and outputs the generated OCT image signal.

The shared optical system 36 may, as in the present embodiment, include a dichroic mirror 64, a slit mirror 66 that has an elliptical, concave reflecting face, an H-galvanometer mirror 68 (whose reflecting surface provides an example of the 'reflecting face' mentioned in the first embodiment), an ellipsoid mirror 70, and a motor 72.

The dichroic mirror 64 guides the SLO light to the slit mirror 66 by causing the SLO light from the polygon mirror 44 of the SLO unit 32 to be transmitted, and guides the signal light to the slit mirror 66 by causing the signal light from the V-galvanometer mirror 60 of the OCT unit 34 to be reflected.

For convenience of explanation, signal light and SLO light are denoted "emitted light" hereafter in a case in which there is no need for the explanation to distinguish between the two.

Figure 5:
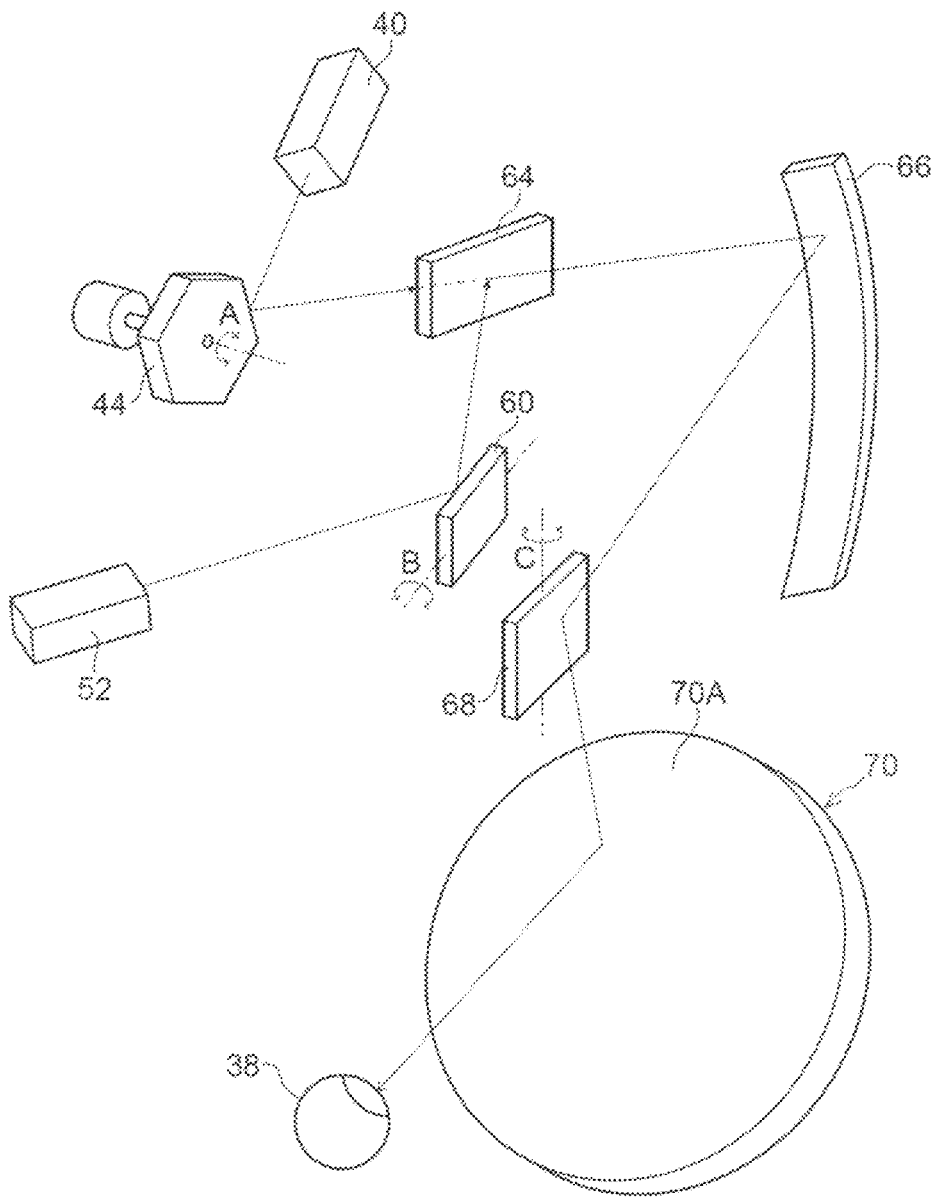
FIG. 5 is schematic perspective view illustrating an example configuration of the optical system in the second embodiment that guides light emitted from respective light sources to the subject's eye.

The slit mirror 66 reflects incident emitted light toward the H-galvanometer mirror 68. The H-galvanometer mirror 68 reflects and sends the emitted light from the slit mirror 66 to a mirror face 70A of the ellipsoid mirror 70. Then, as illustrated in the example of FIG. 5, the H-galvanometer mirror 68 scans the emitted light in an X direction by rotationally oscillating in the arrow C direction on receiving drive force from the motor 48.

The ellipsoid mirror 70 guides emitted light to the retina by reflecting emitted light that was incident to the mirror face 70A (as an example of the 'concave mirror face' mentioned in the first embodiment). Emitted light guided to the retina is reflected by the retina. Then, the retina reflected light is guided to the dichroic mirror 64 in the shared optical system 36, along the same optical path as the emitted light. The dichroic mirror guides the first retina reflected light to the SLO unit 32 and guides the second retina reflected light to the OCT unit 34. Basic configuration of a retinal imaging optical system configured by two elliptical faces is similar to the configurations described in PCT application No. PCT/GB94/02465 (WO 95/13012) and PCT application No. PCT/GB2007/002208 (WO 2008/009877), the contents of which are incorporated herein by reference in their entirety.

During operation of the ophthalmic device 10-2, the controller 3 controls the first retinal image acquisition module 7 (specifically, the rotation of the H-galvanometer mirror 68 via drive signals transmitted to the motor 72, and the rotation of the polygon mirror 44 via drive signals transmitted to the motor 48 in the example of FIG. 4), and the second retinal image acquisition module 1-2 (specifically, the rotation of the H-galvanometer mirror 68 via drive signals transmitted to the motor 72, and the rotation of the V-galvanometer mirror 60 via drive signals transmitted to the motor 62 in the example of FIG. 4) such that the emitted light is scanned, via the slit mirror 66, the H-galvanometer mirror 68 and the ellipsoid mirror 70, across a common imaging region on the retina of the eye 38, for example in a raster pattern. The shape of the common imaging region on the retina is not limited and may, as in the present embodiment, be substantially rectangular (e.g. substantially square), or alternatively a line, for example. As noted above, however, the SLO light from the SLO unit 32 and the signal light from the OCT unit 34 need not be scanned across a common imaging region on the retina, and may instead be scanned across respective imaging regions that are different but nevertheless have a known positional offset relative to one another. For example, in other embodiments, the imaging region imaged by scanning the SLO light may be within the imaging region imaged by scanning the signal light, or vice versa, with the centers of the imaging regions in either case being coincident or offset relative to one another.

In the following, the region of the retina of the eye 38 imaged by the first retinal image acquisition module 7 (e.g. comprising the SLO unit 32, the shared optical system 36 and the SLO image generator 18 in the example of FIG. 4), across which region light from the first retinal image acquisition module 7 (the SLO light in that example) is scanned, is referred to as the "imaging region of the first retinal image acquisition module 7". Similarly, the region of the retina of the eye 38 imaged by the second retinal image acquisition module 1-2 (e.g. comprising the OCT unit 34, the shared optical system 36 and the OCT image generator 16 in the example of FIG. 4), across which region light from the second retinal image acquisition module 1-2 (the signal light in that example) is scanned, is referred to as the "imaging region of the second retinal image acquisition module 1-2". The imaging regions of the first and second retinal image acquisition modules 7 and 1-2 are provided at respective scan locations of the first and second retinal image acquisition modules 7 and 1-2.

As will be described in more detail below, by virtue of the arrangement of components in the shared optical system 36, the first retinal image acquisition module 7 is able to acquire an ultra-wide field (UWF) retinal image as a "reference retinal image", which can be regarded as a 'navigation map' for guiding movement of the imaging regions of the first and second retinal image acquisition modules 7 and 1-2 towards a desired region of the retina, as discussed in more detail below. More particularly, the controller 3 is configured to control movement of the polygon mirror 44 and the H-galvanometer mirror 68 in order to vary the optical path of the SLO light via the slit mirror 66 and the ellipsoid mirror 70 such that the light reflected from the retina and converted by the photo detector 46A produces, as the reference retinal image, up to a 200 degree scan of the retina as measured at the center O of the eye 38. In this way, the UWF retinal image can cover up to about 80% to 85% of the retina. The scanned area of the retina thus has an arc spanning an angle of up to about 200 degrees about the (geometrical) center O of the subject's eye 38. In other embodiments, this angle may be up to 120 degrees, or up to 80 degrees, for example. Whilst the UWF retinal image is being acquired, the first retinal image acquisition module 7 may rotate the direction of the light beam emitted thereby through an angle of at least $\theta$ about the focal point, where $\theta$ is 30 degrees, 60 degrees and 100 degrees, for example.

During the aforementioned changes to the locations of the imaging regions of the first and second retinal image acquisition modules 7 and 1-2, the first retinal image acquisition module 7 is configured to acquire one or more retinal images of regions of the retina whose areas are smaller than the reference imaging area imaged in the reference retinal image.

The device main body controller 13 controls operation of the device main body 12 by exchanging a variety of information with the device main body 12. Moreover, the device main body controller 13 generates a two-dimensional image indicating an aspect of the surface of the retina based on the SLO image signal obtained from the photo detector 46A. The device main body controller 13 also generates a three-dimensional (3D) image of the retina based on tomographic images generated from the OCT image signal from the line sensor 58.

In the present embodiment, the two-dimensional image obtained using the SLO unit 32 is broadly split into a chromatic image based on RG light and an achromatic image based on near-infrared light. Furthermore, tomographic images obtained using the OCT unit 34 are achromatic images. Two-dimensional images obtained using the SLO unit 32 and the tomographic images obtained using the OCT unit 34 may be displayed as still images, or may be displayed as a live view image.

The device main body controller 13 includes the controller 3, an OCT image generator 16, an SLO image generator 18, a user input interface (I/F) 20, at least one user input device 22, a display controller 24, a display 26, a communication I/F 28, and a bus line 30.

The controller 3, the OCT image generator 16, the SLO image generator 18, the user input I/F 20, the display controller 24, and the communication I/F 28 are connected to one another by the bus line 30. Accordingly, the controller 3 can exchange various items of information with the OCT image generator 16, the SLO image generator 18, the user input I/F 20, the display controller 24, and the communication I/F 28.

The controller 3 controls driving of the motors 48, 62 and 72 by controlling respective motor drive circuits (not illustrated in the drawings) corresponding to the motors 48, 62 and 72 via the communication I/F 28.

Furthermore, the controller 3 switches between lighting-up and lighting-out the light source 40A, adjusts the amount of light, changes the wavelength of light produced by the light source 40A, and the like, by controlling a light source drive circuit (not illustrated in the drawings) corresponding to the light source 40A via the communication I/F 28.

Furthermore, the controller 3 switches between lighting-up and lighting-out the SLD 50, adjusts the amount of light, changes the wavelength of light produced by the SLD 50, and the like, by controlling a SLD drive circuit (not illustrated in the drawings) corresponding to the SLD 50 via the communication I/F 28.

Furthermore, the controller 3 controls operation of the bandpass filter 40B, operation of the optical filter 46B, and operation of the reference mirror of the reference light optical system 54 via the communication I/F 28.

The at least one user input device 22 may, as in the present embodiment, include a keyboard and a mouse, and is operable to receive various instructions from a user. The user input device 22 may additionally or alternatively include a touch panel, or the like.

The user input devices 22 are connected to the user input I/F 20, and are arranged to output an instruction content signal indicating contents of the received instructions to the user input I/F 20. The controller 3 is configured to execute processing operations in accordance with the instruction content signal input from the user input I/F 20.

The display 26 may, for example, be an LCD or organic electroluminescence display (OELD). The display 26 is connected to the display controller 24. Under the control of the controller 3, the display controller 24 controls the display 26 so as to display on the display 26 a two-dimensional image obtained using the SLO unit 32 and a 3D representation of the retina based on tomographic images obtained using the OCT unit 34. Under the control of the controller 3, the display controller 24 can also display various screens, such as menu screens, by controlling the display 26.

The communication I/F 28 is connected to an electrical system of a device main body 12, and operates under the control of the controller 3 to govern exchange of various information between the controller 3 and the device main body 12.

The SLO image generator 18 acquires the SLO image signal from the photo detector 46A of the SLO unit 32 via the communication I/F 28, and may, as in the present embodiment, be a dedicated circuit configured to perform processing operations to generate a two-dimensional image based on the acquired SLO image signal.

The SLO image generator 18 may, as in the present embodiment, be configured to output frames of the generated two-dimensional images to the display controller 24 at a frame rate of typically tens of frames per second in the live tracking SLO feed. The display controller 24 may display the two-dimensional images input from the SLO image generator 18 on the display 26 as a live image in accordance with instructions by the controller 3. Moreover, the display controller 24 may display the two-dimensional images input from the SLO image generator 18 on the display 26 as still images, in accordance with instructions by the controller 3.

The OCT image generator 16 is configured to acquire the OCT image signal from the line sensor 58 of the OCT unit 34 via the communication I/F 28, and may, as in the present embodiment, be a dedicated circuit configured to perform processing operations to generate tomographic images based on the acquired OCT image signal.

The OCT image generator 16 may, as in the present embodiment, be configured to generate a 3D image of the retina by combining tomographic images (which may also be acquired at a rate of typically tens of frames per second) using image processing techniques known to those skilled in the art. The tomographic images represent 'slices' through the retina at different depths from the retinal surface, and are combined by the OCT image generator 16 to generate a 3D image of the imaged portion of the retina. The display controller 24 may display the 3D image input from the OCT image generator 16 on the display 26, in accordance with instructions from the controller 3.

Although the OCT image generator 16 and the SLO image generator 18 are each implemented by a computer that includes a CPU, ROM, and RAM in the present embodiment, the technology disclosed herein is not limited thereto, and one or both of the OCT image generator 16 and the SLO image generator 18 may alternatively be implemented by field-programmable gate arrays (FPGA), or may be implemented by an application-specific integrated circuit (ASIC). Moreover, the OCT image generator 16 and the SLO image generator 18 may each be implemented by a combination of hardware configuration and software.

Figure 6:
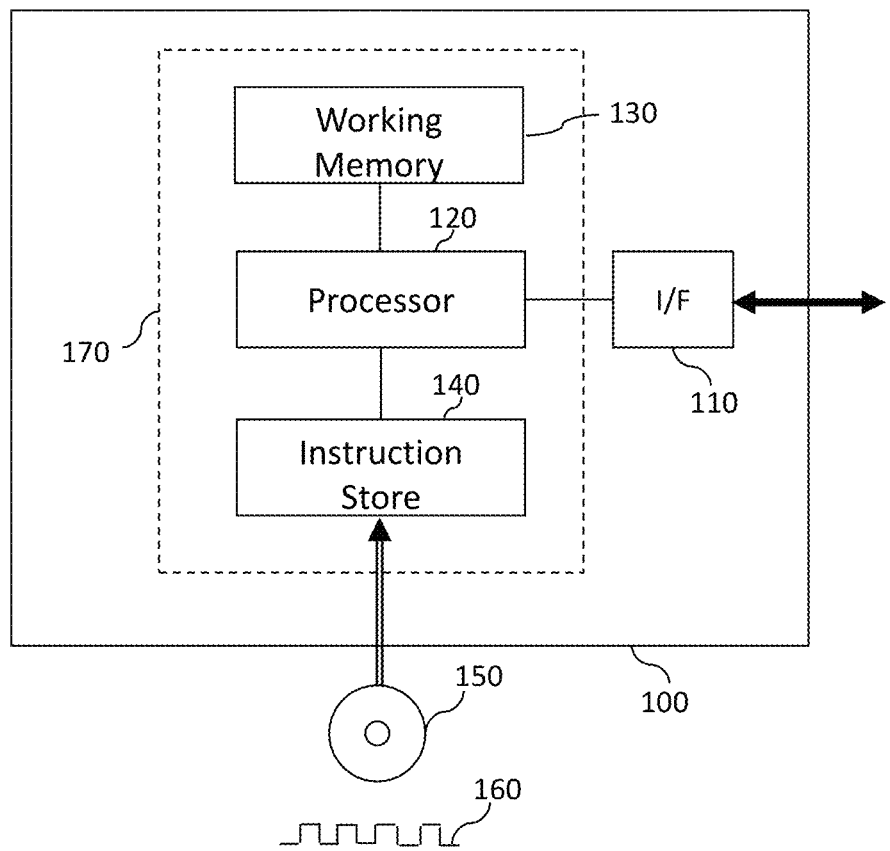
FIG. 6 is a block diagram illustrating an example of hardware configuration of the controller included in an ophthalmic device according to an embodiment.

FIG. 6 shows an exemplary implementation of the controller 3, in programmable signal processing hardware. The signal processing apparatus 100 shown in FIG. 6 comprises a communication I/F 110 for receiving data from, and transmitting control signals to, the bus 30. The signal processing apparatus 100 further comprises a processor (CPU) 120 for controlling the overall operation of the ophthalmic device 10-2, a working memory 130 (e.g. a random access memory) and an instruction store 140 storing computer-readable instructions which, when executed by the processor 120, cause the processor 120 to perform the processing operations hereinafter described to control the ophthalmic device 10-2. The instruction store 140 may comprise a ROM (e.g. in the form of an electrically-erasable programmable read-only memory (EEPROM) or flash memory) which is pre-loaded with the computer-readable instructions. Alternatively, the instruction store 140 may comprise a RAM or similar type of memory, and the computer-readable instructions can be input thereto from a computer program product, such as a computer-readable storage medium 150 such as a CD-ROM, etc. or a computer-readable signal 160 carrying the computer-readable instructions.

In the present embodiment, the combination 170 of the hardware components shown in FIG. 6, comprising the processor 120, the working memory 130 and the instruction store 140, is configured to implement the functionality of the controller 3 and, in particular, the functions of the pupil alignment module 2, the pupil alignment maintenance module 3-2, the retina scan location alignment module 4-2, and the retina scan location maintenance module 5-2, which will now be described in detail with reference to FIGS. 7 to 15.

Figure 7:
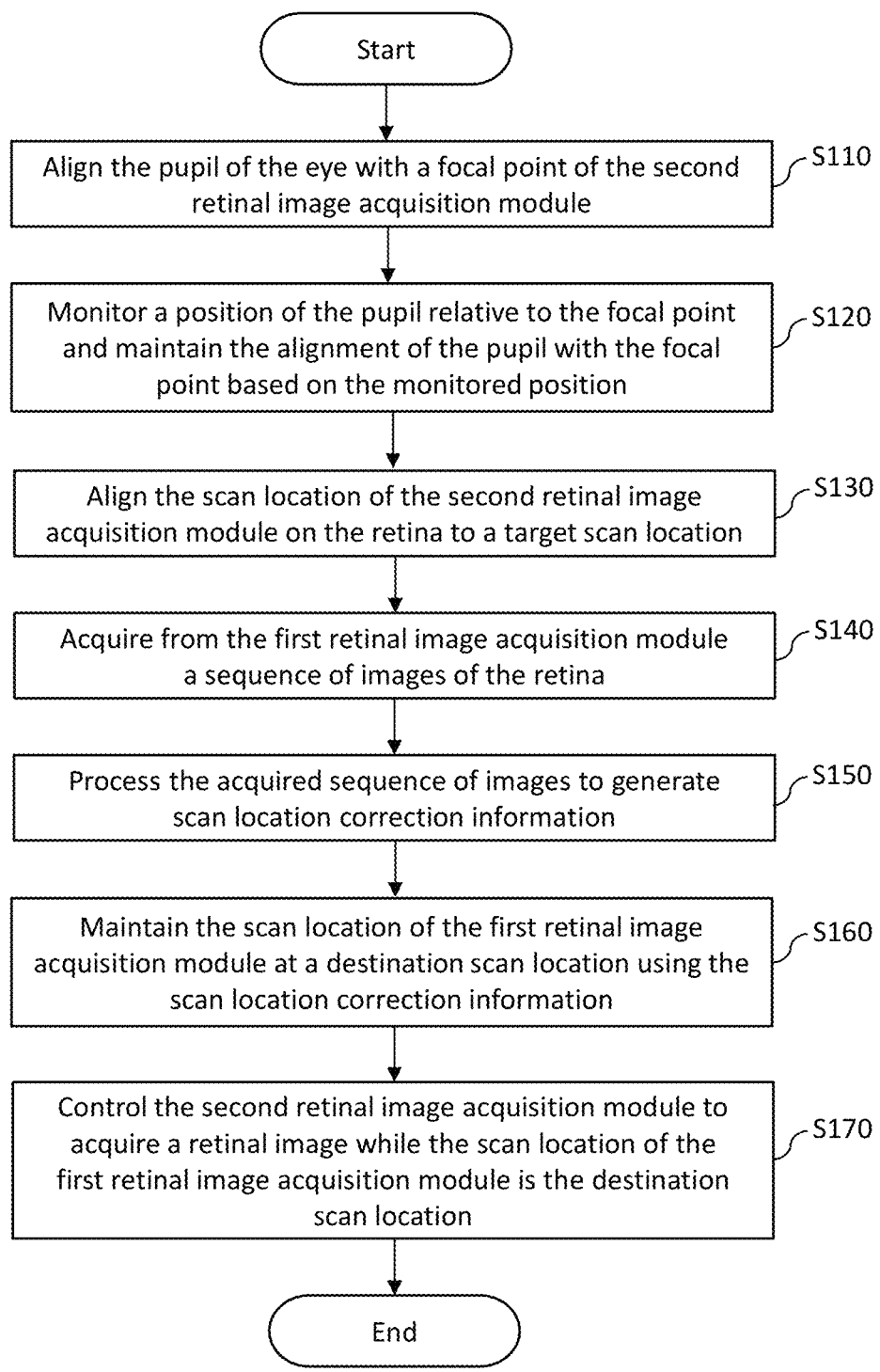
FIG. 7 is a flow diagram illustrating a method of operating the ophthalmic device of the second embodiment.

FIG. 7 is a flow chart illustrating a method of operating the ophthalmic device 10-2 to perform a scan at a target scan location on the retina so as to illuminate and acquire an OCT image of a region of the retina at the target scan location.

Prior to the performance of this method, the target scan location may be acquired. To this end, the controller 3 may control the first retinal image acquisition module 7 to acquire the above-mentioned reference retinal image. During this process, the target display module 6 operates in the static fixation mode to display a fixation target for fixing the gaze of the subject's eye 38 in a central gaze direction. Then, RG light is emitted from the light source 40A of the SLO unit 32, and the UWF retinal image of the subject's eye 38 is captured by operation of the SLO unit 32 and the shared optical system 36, under the control of the controller 3. An UWF RG-SLO image is acquired from the SLO image generator 18 as an example of the reference retinal image. It should be noted that near-infra red light from the light source 40A may alternatively be used to acquire an UWF IR-SLO image as the reference retinal image.

The patient's gaze direction may, as in the present embodiment, remain fixed during all of the subsequently imaging processes described below, where the ophthalmic device 10-2 is operable to image the different regions of the retina shown in the UWF reference retinal image without the patient changing the gaze direction. During these imaging processes, the controller 3 may monitor a live tracking SLO feed from the first retinal image acquisition module 7 to measure a motion metric that is indicative of the quality of the fixation, and generate signals for causing visual cues (e.g. changing colour of the fixation target, blinking the fixation target or changing a pattern of the fixation target) to be displayed to the subject for improving the fixation, as necessary.

Figure 8:
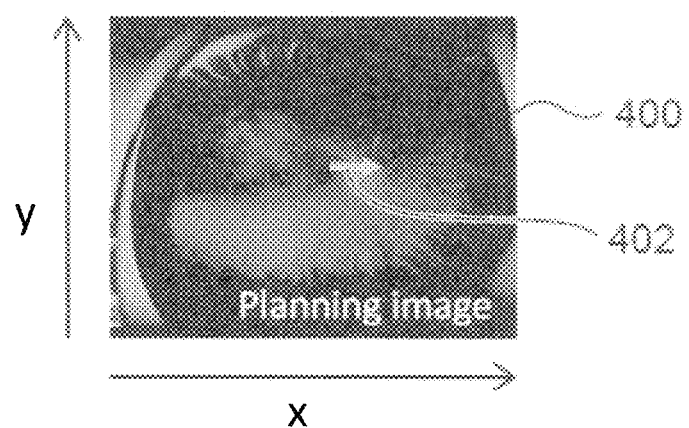
FIG. 8 is a schematic of a reference retinal image acquired by the first retinal image acquisition module of the second embodiment.

Under control of the controller 3, the display controller 24 controls the display 26 to display the acquired reference retinal image 400 (also referred to herein as a "planning image"), as illustrated in FIG. 8. The user is then able to view the UWF reference retinal image 400 (hereafter referred to as the "UWF retinal image 400") on the display 26, and identify a region of interest where, for example, a sign of a disorder is suspected and in which it would be desirable to perform OCT.

The controller 3 designates a target in the UWF retinal image 400 which corresponds to the target scan location on the retina. The target may be designated by the controller 3 anywhere in the UWF retinal image 400 (including the peripheral portion of the retina), in one of a number of different ways. By way of an example, in the present embodiment, the user moves a cursor 402 overlaid on the displayed UWF retinal image 400, using the input device 22 (e.g. by moving the mouse). The user can designate a point of interest on the displayed UWF retinal image 400 in any desirable way, for example by clicking a button on the mouse while the cursor 402 is located at that point. The controller 3 designates the target by recording, for example, pixel locations in the UWF retinal image 400, which correspond to the location in the UWF retinal image 400 of the cursor 402 when the user designation (e.g. the mouse click) occurred. A region of the UWF retinal image 400 surrounding the target is thus selected for OCT imaging.

Although the target is thus designated based on the selection of a point on the displayed UWF retinal image 400 by the user in the present embodiment, the target may alternatively be designated based on the designation by the user of a line or two-dimensional region in the UWF retinal image 400 (e.g. by a 'click, drag and release' operation on the mouse to define e.g. a box in the UWF retinal image 400). For example, where a two-dimensional region in the UWF retinal image 400 is selected by the user, the controller 3 may designate the target as the coordinates (in the coordinate system of the of the UWF retinal image 400) of the centroid (geometrical center) of the two-dimensional region. The size of the two-dimensional region selected by the user may be used to define the size of the imaging area on the retina. The target may alternatively be designated automatically by the controller 3 using e.g. pattern-matching algorithms to identify one or more regions of interest (where features usually associated with a disorder are located) in the reference retinal image 400.

In process S110, the pupil alignment module 2 aligns the pupil of the eye with the focal point of the second retinal image acquisition module 1-2. This process is substantially the same as process S10 described above with reference to FIG. 2, and will therefore not be described further here.

Following the alignment of the pupil with the focal point, the ophthalmic device 10-2 starts a procedure for performing a scan of a part of the retina, and the target display module 6 switches from operating in the static fixation mode to operating in the dynamic fixation mode.

When an OCT image or the like is captured over an ultra-wide angle region, namely, in a case in which the capturing target region of the OCT image is a peripheral portion of the subject's eye 38, the optical axis of light emitted from the SLD 50 for capturing the OCT image is liable to depart from the pupil of the subject's eye 38, and the quality of the OCT image is liable to deteriorate due to the vignetting that is caused by misalignment of the pupil with the focal point.

Thus, in process S120, the pupil alignment maintenance module 3-2 begins to monitor the position of the pupil relative to the focal point and maintain the alignment of the pupil with the focal point based on the monitored position. The pupil alignment maintenance module 3-2 may, as in the present embodiment, receive from the first retinal image acquisition module 7 an image of a subject's eye 38, determine whether or not at least a portion of a pupil region of the received image is within a predetermined permissible region within the received image, and generate an output signal that is indicative of the determination, the pupil region being an image of at least a portion of the pupil of the eye 38. The pupil alignment maintenance module 3-2 may alternatively determine whether or not a proportion of a predetermined permissible region of the received image that is occupied by at least a portion of a pupil region of the received image is a predetermined threshold value or greater, and generate an output signal that is indicative of the determination. The output signal may be used to generate and display a warning message (or provide another, e.g. audio and/or visual) indication to alert the subject and/or the operator that the alignment of the pupil with the focal point is unsatisfactory, so that remedial action can be taken. The output signal may alternatively be used for closed-loop control of the relative positioning of the pupil and focal point by the pupil alignment maintenance module 3-2, in order to automatically compensate for any misalignment of the pupil and the focal point that may be caused by the movement of the subject.

The pupil alignment maintenance module 3-2 may be arranged to generate a binary image by binarising the received image of the subject's eye 38. In some embodiments, the pupil alignment maintenance module 3-2 may be arranged to generate a determination-use image by removing from the received image (or from the binary image, in embodiments in which the aforementioned binary image is generated) an unneeded region other than a received image pupil region, the received image pupil region being an image of at least a portion of the pupil in the received image (or in the binary image, as the case may be); in those embodiments, the pupil alignment maintenance module 3-2 is arranged to perform the determination based on the determination-use image.

Figure 9:
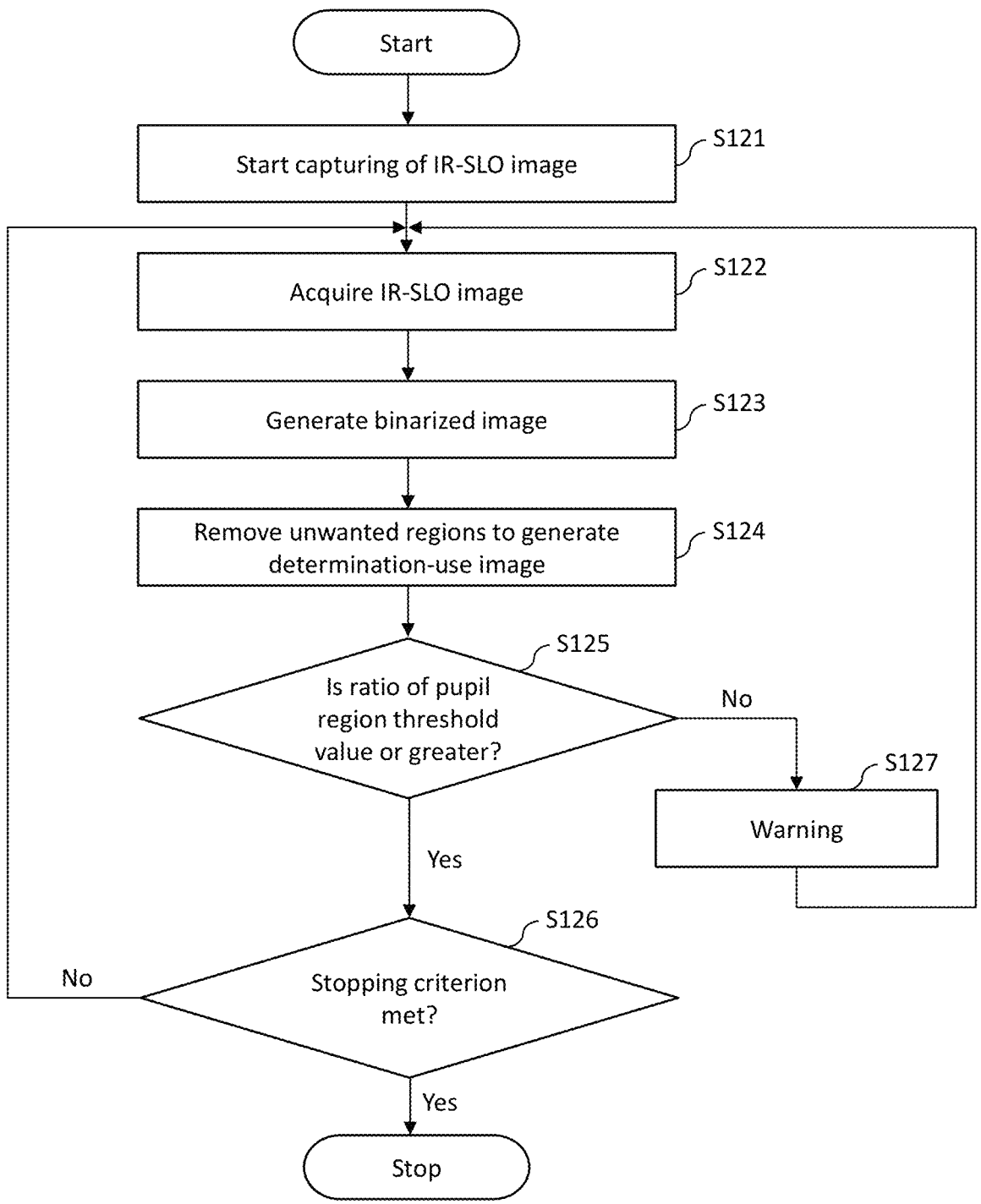
FIG. 9 is a flowchart illustrating an example of pupil position determination processing.

An example of a process by which the pupil alignment maintenance module 3-2 may maintain the alignment of the pupil with the focal point will now be described with reference to FIG. 9.

First, in process S121, capturing of IR-SLO images by the first retinal image acquisition module 7 is started. Namely, near-infrared light is emitted from the light source 40A, the SLO unit 32 is controlled such that the target scan location on the retina, which corresponds to the designated target in the UWF retinal image 400, is scanned, and narrow-range IR-SLO images are captured. Although explanation is given regarding a case in which IR-SLO images are captured in the present embodiment, RG-SLO images (or other kind of images) may be captured.

In process S122, the pupil alignment maintenance module 3-2 acquires the narrow-range IR-SLO image captured by the first retinal image acquisition module 7.

Figure 10:
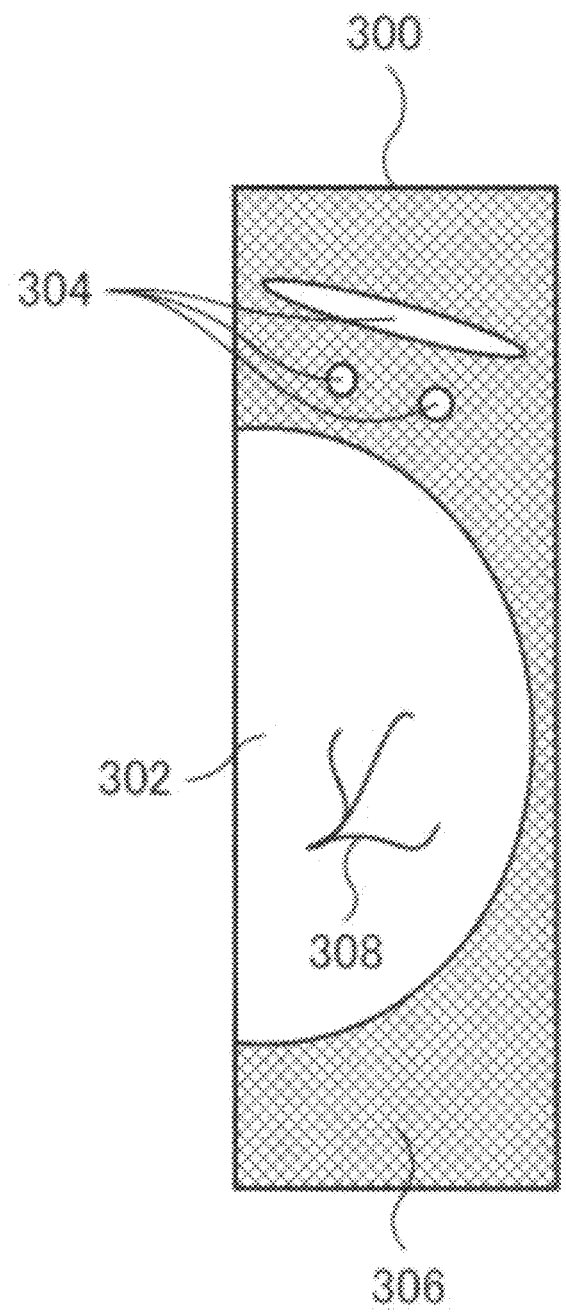
FIG. 10 is a diagram illustrating an example of a binarized image.

In process S123, binarization processing is optionally executed on the acquired IR-SLO image, so that a binarized image may be generated. For example, for each pixel of the IR-SLO image, a white pixel is given if the pixel value is a predetermined binarization threshold value or greater, and a black pixel is given if the pixel value is less than the binarization threshold value. FIG. 10 illustrates an example of such a binarized image.

White regions in the binarized image 300 illustrated in FIG. 10 are regions onto which reflected light of light for IR-SLO imaging emitted toward the subject's eye 38 has been detected, and a white region 302 therein represents the pupil region of the subject's eye. Moreover, white regions 304 are regions other than the pupil, for example, an eyelash or eyelid region. Note that the white region 302 and the white regions 304 are sometimes connected. Moreover, a black region 306 is a region where the reflected light of the light for IR-SLO imaging emitted toward the subject's eye 38 has not been detected. As illustrated in FIG. 10, for example, a black region 308 such as a blood vessel sometimes appears in the white region 302 representing the pupil region.

Thus, sometimes white regions represent not only the pupil region, but also eyelash and eyelid regions. However, eyelash and eyelid white regions 304 are regions that are not needed in a case in which determining whether or not the position of the pupil is within the permissible range. Moreover, the black region 308 such as a blood vessel that has appeared in the white region 302 representing the pupil region is also a region not needed in a case in which determining whether or not the position of the pupil is in the permissible range.

Thus, in process S124, the pupil alignment maintenance module 3-2 optionally generates a determination-use image by removing unwanted regions other than the pupil from the binarized image 300 generated in process S123 (or from the received image, in cases where binarization is not performed). In other words, the pupil alignment maintenance module 3-2 generates the determination-use image by removing from the binarized image 300 an unneeded region other than a binary image pupil region, the binary image pupil region being an image of at least a portion of the pupil in the binarized image 300.

More specifically, for example, the white region 304 and the black region 308, which are unwanted regions, are removed from the binarized image 300 by executing known morphological operations on the binarized image 300.

Figure 11:
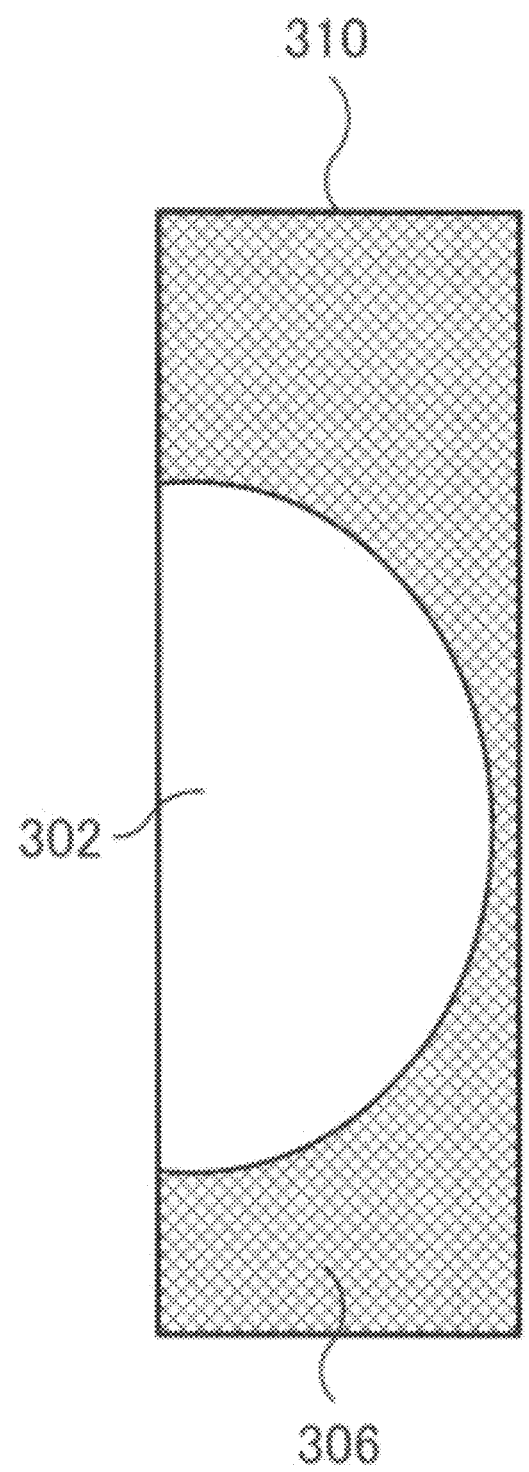
FIG. 11 is a diagram illustrating an example of a determination-use image.

Here, morphological operations is processing that leaves a feature portion of an image (the pupil in the present exemplary embodiment) and removes other unwanted regions by repeatedly performing downscale processing and upscale processing on a processing-target image. By executing such morphological operations on the binarized image 300, a determination-use image 310 from which the unwanted regions have been removed is generated, as illustrated in FIG. 11. Note that although explanation has been given regarding a case in which unwanted regions are removed by morphological operations in the present exemplary embodiment, the processing that removes unwanted regions is not limited to morphological operations. For example, the unwanted regions may be removed using known feature extraction processing, pattern matching processing, or the like.

In process S125, the pupil alignment maintenance module 3-2 determines whether or not at least a portion of a pupil region of the determination-use image 310 is within a predetermined permissible region within the determination-use image 310 (the pupil region being an image of at least a portion of the pupil of the subject's eye 38). Thus, a determination is made as to whether or not the position of the pupil is in the permissible range based on the determination-use image 310 generated in process S124.

Figure 12:
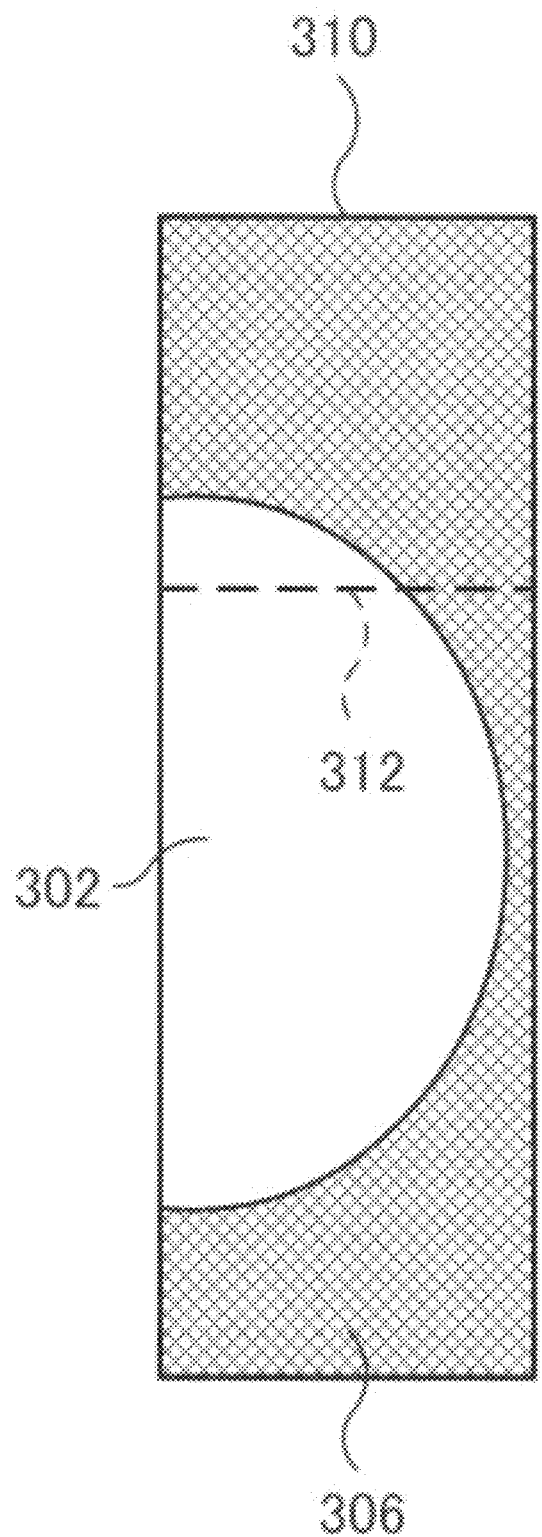
FIG. 12 is a diagram illustrating an example of a determination region in a determination-use image.

The pupil alignment maintenance module 3-2 may alternatively determine whether or not a proportion of a predetermined permissible region of the determination-use image 310 that is occupied by at least a portion of a pupil region of the determination-use image 310 is a predetermined threshold value or greater. In other words, a determination may be made as to whether or not a ratio of a region occupied by the pupil in a predetermined determination region of the determination-use image 310 is a predetermined threshold value or greater. The determination region in the present exemplary embodiment is set to, for example, a line 312 running along a width direction (the X direction) of the determination-use image 310, as illustrated in FIG. 12. Then, determination is made as to whether or not the ratio of the number of pixels occupied by white pixels (pixels representing the pupil) on the line 312 to the total number of pixels on the line 312 is the threshold value or greater. Here, the threshold value is set to a value such that the quality of the subsequently imaged OCT image will be in a permissible range when the number of white pixels is the threshold value or greater.

In a case in which the ratio of the number of pixels occupied by white pixels on the line 312 to the total number of pixels on the line 312 is the threshold value or greater, the processing proceeds to process S126, where it is determined whether or not a stopping criterion is met. The stopping criterion may, for example, be that OCT imaging by the second retinal image acquisition module 1-2 has been completed. If the stopping criterion is met, then the processing stops, otherwise the processing transitions back to process S122. Alternatively, if the ratio is determined in process S125 to be less than the threshold value, the processing transitions to process S127.

In process S127, the pupil alignment maintenance module 3-2 generates an output signal that is indicative of the determination in process S127. The primary controller 14 may control the display controller 24, on the basis of the output signal generated by the pupil alignment maintenance module 3-2, to set the display content that is displayed on the display 26, for example to display a warning message stating that the OCT image will not be imaged normally. The operator then instructs the patient to look at the fixation target. The output signal may thus be used to correct the position of the subject's eye 38 relative to the focal point so as to keep the pupil position in alignment with the focal point.

Alternatively, in process S127, the pupil alignment maintenance module 3-2 may use the generated output signal to control an XYZ stage or the like of the ophthalmic device 10-2 so as to adjust the positioning of the focal point of the ellipsoid mirror 70 relative to the pupil of the eye 38 in order to compensate for movements of the eye 38 and thus maintain the alignment of the pupil with the focal point. Following the execution of process S127, processing transitions back to process S122, and another acquired IR-SLO image is processed as described above.

Figure 13:
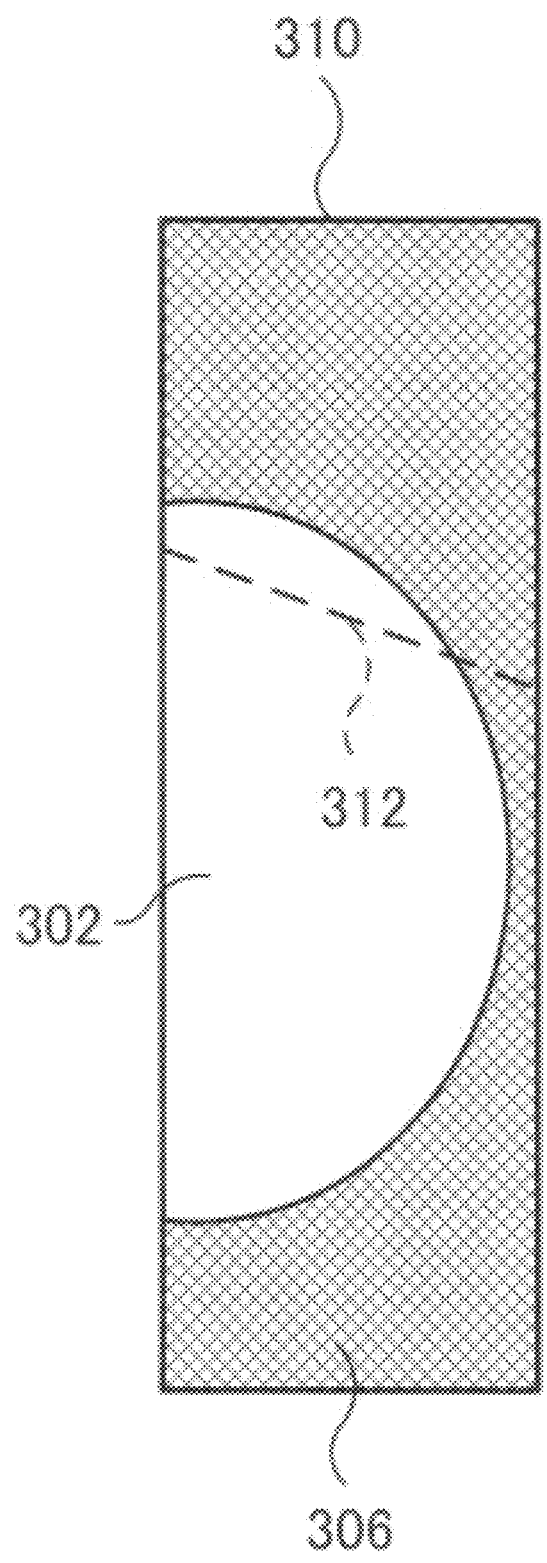
FIG. 13 is a diagram illustrating an example of a determination region in a determination-use image.
Figure 14:
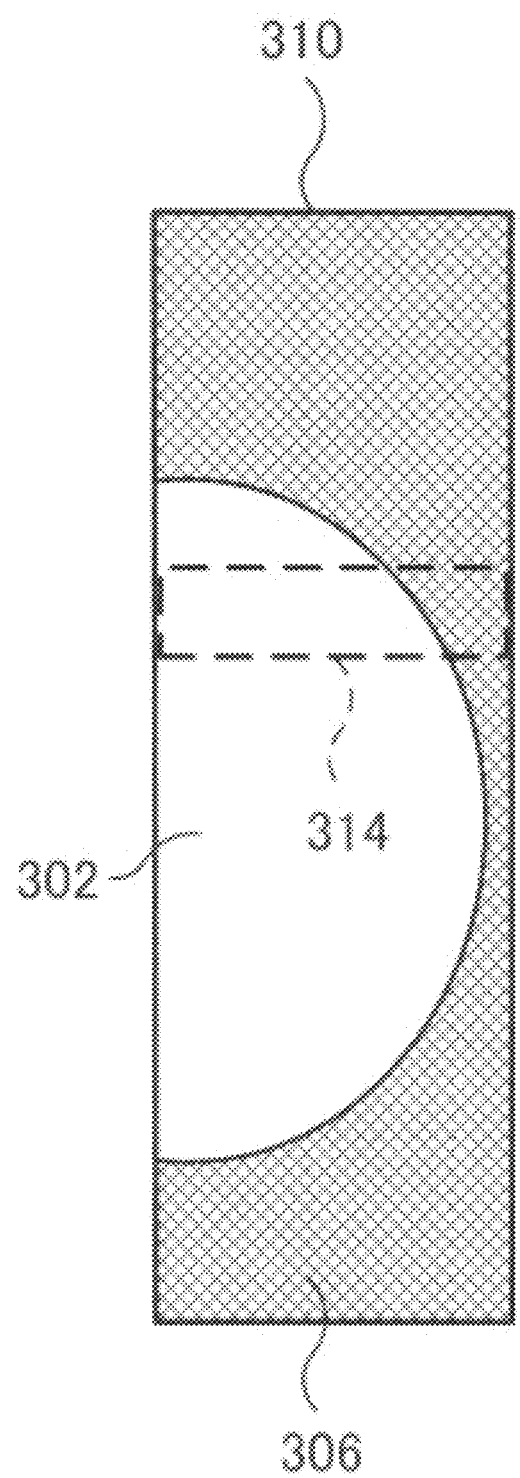
FIG. 14 is a diagram illustrating an example of a determination region in a determination-use image.
Figure 15:
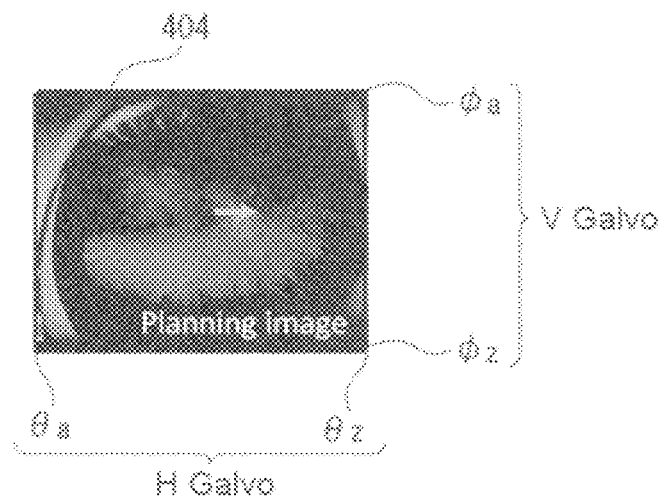
FIG. 15 is a schematic of a look-up table used by the controller to determine scan angles for the H-galvanometer mirror and V-galvanometer mirror of the ophthalmic device based on positions in the reference retinal image.

Note that although the line 312 in FIG. 12 is a line along the width direction of the determination-use image 310, the line 312 may be inclined with respect to the width direction of the determination-use image 310, as illustrated in FIG. 13. Moreover, the determination region may be a rectangular region 314, as illustrated in FIG. 14. Moreover, the determination region may be a freely selected polygonal region other than that of a rectangle.

Further details of the pupil position determination processing described above with reference to FIGS. 9 to 13 are provided in the applicant's co-pending application titled "Ocular Image Capturing Device", which was filed on the same date as the present application with agent reference number 198 411, the contents of which are incorporated herein by reference in their entirety. At least some of the features of this cross-referenced disclosure may be claimed in the present application.

Referring again to FIG. 7, in process S130, the controller 3, functioning as the retina scan location alignment module 4-2, aligns the scan location of the second retinal image acquisition module 1-2 on the retina with the target scan location. Process S130 is performed while the alignment of the pupil with the focal point is being maintained by the pupil alignment maintenance module 3-2. The controller 3 may align the scan location of the second retinal image acquisition module 1-2 on the retina to the target scan location by determining an offset indicator that is indicative of an offset between a designated scan location of the first retinal image acquisition module 7 on the retina and an initial scan location of a scan performed by the first retinal image acquisition module 7, and controlling the first retinal image acquisition module 7, based on the determined offset indicator, to move the scan location of the first retinal image acquisition module 7 from the initial scan location to a destination scan location that is closer to the designated scan location than is the initial scan location, the target scan location of the second retinal image acquisition module 1-2 being the scan location of the second retinal image acquisition module 1-2 while the scan location of the first retinal image acquisition module 7 is the destination scan location.

In more detail, the controller 3 controls the first retinal image acquisition module 7 to acquire a current retinal image of an initial imaging region of the retina that is within the reference imaging area. For this purpose, the controller 3 may, as in the present embodiment, employ a look-up table (as shown at 404 in FIG. 15) stored in the instruction store 140, which correlates pixel locations in the UWF retinal image 400 with corresponding inclination angles θ of the H-galvanometer mirror (H-Galvo) 68 and φ of the V-galvanometer mirror (V-Galvo) 60 that were set while image information at those points was acquired during the imaging process. Where such a look-up table is used, the controller 3 may look up the scan angles θ and φ associated with a pre-stored point that is closest to the target in the reference retinal image, and control the drive of the H-Galvo 68 and V-Galvo 60 to deflect the SLO light across angular ranges centered on those scan angles, the angular ranges of the scan defining the size of the imaged region of the retina. In this way, the emitted light may be scanned over an imaging region on the retina which is close to the intended imaging region, corresponding to that centered on the designated target. For a more precise setting of the initial imaging region, the scan angles may be determined by extrapolating between the values in the look-up table. It should be noted, however, that such initial setting of the scan angles to image the initial imaging region within the reference imaging area may be omitted, and the scan angles θ and φ may alternatively be set to any other values that allow an initial imaging region within the reference imaging area to be imaged.

The controller 3 then uses target, and the UWF retinal image 400 as a 'global map', to move the imaging region of the first retinal image acquisition module 7 from the initial imaging region to a destination imaging region on the retina, and controls the first retinal image acquisition module 7 to acquire a retinal image of the destination imaging region. Along the way, the controller 3 may use one or more retinal images acquired by the first retinal acquisition module 7 to 'land-mark' the current position(s) of the images on the global map, allowing it to determine any further adjustments to the location of the imaging region that might be required to arrive at the destination imaging region. The controller 3 can thus move the imaging region to the destination imaging region of interest in a step-wise manner, without the need for scan location mappings of the kind present in the look-up table 404, and without being influenced by scan location errors due to systematic variations in the optical imaging system and fixation errors. More particularly, the controller 3 may control the first retinal image acquisition module 7 to acquire a retinal image of a destination imaging region of the first retinal image acquisition module 7 by performing at least once the sequence of processes S42 to S48 that are described with reference to FIG. 5B in the applicant's co-pending application titled "Ophthalmic Device", which was filed on the same date as the present application with agent reference number 198 408, the contents of which are incorporated herein by reference in their entirety. At least some of the features of this cross-referenced disclosure may be claimed in the present application.

The retina scan location maintenance module 5-2 then maintains the scan location of the second retinal image acquisition module 1-2 at the target scan location by performing, while the alignment of the pupil with the focal point is being maintained by the pupil alignment maintenance module 3-2, processes S140 to S160 shown in FIG. 7, as follows.

In process S140, the retina scan location maintenance module 5-2 acquires from the first retinal image acquisition module 7 a sequence of images of the retina while the scan location of the first retinal image acquisition module 7 is set to the destination scan location.

In process S150, the retina scan location maintenance module 5-2 processes the acquired images to generate scan location correction information. The retina scan location maintenance module 5-2 may, as in the present embodiment, process the sequence of images to generate, as the scan location correction information, retinal position tracking information that is indicative of a movement of the retina during the acquisition of the sequence images. In this case, the retina scan location maintenance module 5-2 processes the sequence of images being processed by: (i) receiving at least one image of the retina; (ii) calculating a cross-correlation between a reference image and an image based on the at least one received image to acquire an offset between the image and the reference image; and repeating processes (i) and (ii) to acquire, as the retinal position tracking information, respective offsets for the images in the sequence.

In process S160, the retina scan location maintenance module 5-2 maintains the scan location of the first retinal image acquisition module 7 at the destination scan location using the generated scan location correction information, and thus maintains the location of the second retinal image acquisition module 1-2 at the target scan location. More particularly, the retina scan location maintenance module 5-2 may maintain the scan location of the first retinal image acquisition module 7 at the destination scan location by using the generated retinal position tracking information to control the drive of the H-Galvo 68 and V-Galvo 60 to keep the SLO light scan substantially at the destination scan location and thus at least partially compensate for eye movements. The retina scan location maintenance module 5-2 may alternatively control the target display module 6, based on the retinal position tracking information, to vary a characteristic of the displayed target (e.g. its colour) so as to maintain the gaze direction of the subject's eye and keep the scan location steady.

Advantageous methods of processing the sequence of retinal images to generate retinal position tracking information, which is indicative of a movement of the retina during the acquisition of the sequence of images, are described in the applicant's co-pending application titled "Retinal Position Tracking", which was filed on the same date as the present application with agent reference number 198 407, the contents of which are incorporated herein by reference in their entirety. In brief, a processing method described in that application comprises modifying the reference image while processes (i) and (ii) are being repeated, by determining a measure of similarity between correspondingly located regions of pixels in two or more of the received images and accentuating features in the reference image representing structures of the imaged retina in relation to other features in the reference image based on the determined measure of similarity. At least some of the features of the processing methods described in this cross-referenced application may be claimed in the present application.

In process S170 shown in FIG. 7, the controller 3 controls the second retinal image acquisition module 1-2 to acquire a retinal image while the scan location of the first retinal image acquisition module 7 remains at the destination scan location. By way of an example, the controller 3 may control the second retinal image acquisition module 1-2 to illuminate and acquire a 3D image of the current imaging region of the second retinal image acquisition module 1-2, by acquiring a plurality of tomographic images of the current imaging region (over a period of about 1-2 seconds) and processing the tomographic images by the OCT image generator 16 to generate the 3D image.

During the acquisition of the plurality of tomographic images by the second retinal image acquisition module 1-2 in process S170, the first retinal image acquisition module 7 may operate in a live tracking mode to acquire one or more further images of the retina as "post-registration image(s)" while the imaging region of the first retinal image acquisition module 7 remains as previously set.

The controller 3 may then generate a marker retinal image based on the one or more retinal images, and may also generate a comparison image based on at least a portion of the UWF retinal image 400. The marker retinal image may correspond to a single post-registration image acquired by the first retinal image acquisition module 7 while the second retinal image acquisition module 1-2 is acquiring the plurality of tomographic images, or may be obtained by processing two or more post-registration images acquired by the first retinal image acquisition module 7 while the second retinal image acquisition module 1-2 is acquiring the tomographic images, for example by calculating an average of two or more of the post-registration images, or selecting an image from a plurality of post-registration images according to a selection criterion such as image quality. The comparison image may, as in the present embodiment, correspond to the entire UWF retinal image 400, or may alternatively be only a portion of the UWF retinal image 400 (e.g. covering an area of the retina in which retinal scans are most likely to be made). The controller 3 may then compare the marker retinal image with the comparison image 400 and, based on the comparison, generate a marker that is indicative of the position of the marker retinal image within the comparison image. The controller 3 may generate the maker on the basis of a calculated cross-correlation between the marker retinal image and the comparison image, for example.

The controller 3 may then store the marker in association with the comparison image. The marker may be stored not only in association with the comparison image but additionally or alternatively in association with one or more of: (i) the (3D) retinal image acquired by the second retinal image acquisition module 1-2; (ii) at least one of the one or more post-registration retinal images acquired by the first retinal image acquisition module 7; (iii) the marker retinal image; (iv) the reference retinal image 400; and (v) a clipped region of the reference retinal image 400, wherein the clipped region is positioned at the determined position of the marker retinal image within the reference retinal image 400, and may be same size as (or preferably larger than) the post-registration image(s).

Modifications and Variations

Many modifications and variations can be made to the embodiments described above.

In the embodiments explained above, the polygon mirror 44 arranged to scan in the Y direction, and the V-galvanometer mirror 60 arranged to scan in the Y direction, are disposed at the light incidence side of the dichroic mirror 64. However, the dichroic mirror 64 may be disposed in a position separated in the optical axis direction from the focal point of the slit mirror 66, and the polygon mirror 44 or the V-galvanometer mirror 60 that scans in the Y direction may be disposed at the focal point position of the slit mirror 66. In such cases, the polygon mirror 44 or the V-galvanometer mirror 60 functions as a shared scanning optical system employed during SLO image acquisition and OCT image acquisition.

Furthermore, although an example has been described in which a shared optical axis, along which light for SLO and light for OCT passes, is generated by the dichroic mirror 64, a beam splitter such as a polarizing beam splitter or an optical member such as a half-mirror may be employed instead of the dichroic mirror 64.

Figure 16:
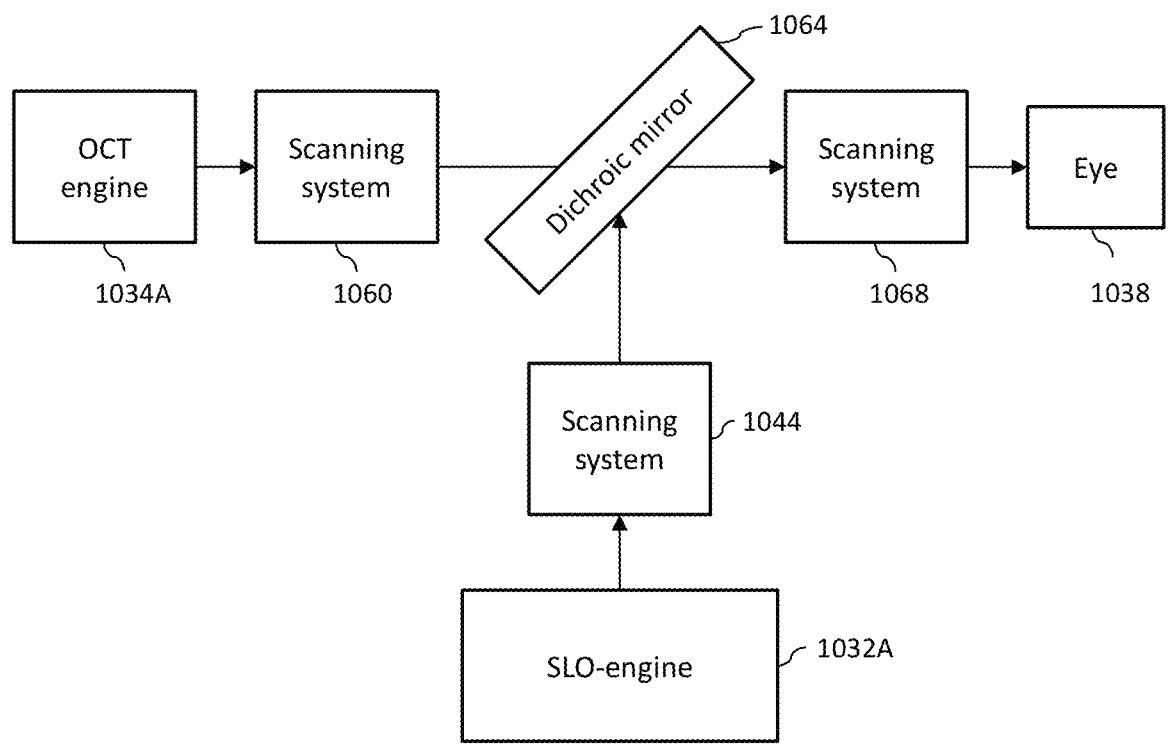
FIG. 16 is a schematic illustration of the optical system of the ophthalmic device of the second embodiment.

In the above embodiments, the polygon mirror 44 and the V-galvanometer mirror 60 are disposed at the light incidence side of the dichroic mirror 64, and the H-galvanometer mirror 68 for X direction scanning, shared by SLO and OCT, is disposed at the light emission side of the dichroic mirror 64, as illustrated in FIG. 4. FIG. 16 illustrates a configuration corresponding to the SLO unit 32, the OCT unit 34, and the shared optical system 36 illustrated in FIG. 4. As illustrated in FIG. 16, a device main body includes a dichroic mirror 1064, an SLO engine 1032A, and an OCT engine 1034A. A scanning system 1044 is disposed between the dichroic mirror 1064 and the SLO engine 1032A. Further, another scanning system 1060 is disposed between the dichroic mirror 1064 and the OCT engine 1034A. A further scanning system 1068 is disposed between the dichroic mirror 1064 and a subject's eye 1038.

Note that the scanning system 1044 corresponds to the polygon mirror 44, and the SLO engine 1032A is a portion obtained by removing the polygon mirror 44 from the SLO unit 32 in FIG. 4. The scanning system 1060 corresponds to the V-galvanometer mirror 60, and the OCT engine 1034A is a portion obtained by removing the V-galvanometer mirror 60 from the OCT unit 34 in FIG. 4. The scanning system 1068 corresponds to the H-galvanometer mirror 68.

The following modifications can be can be made to the scanning optical system.

Figure 17:
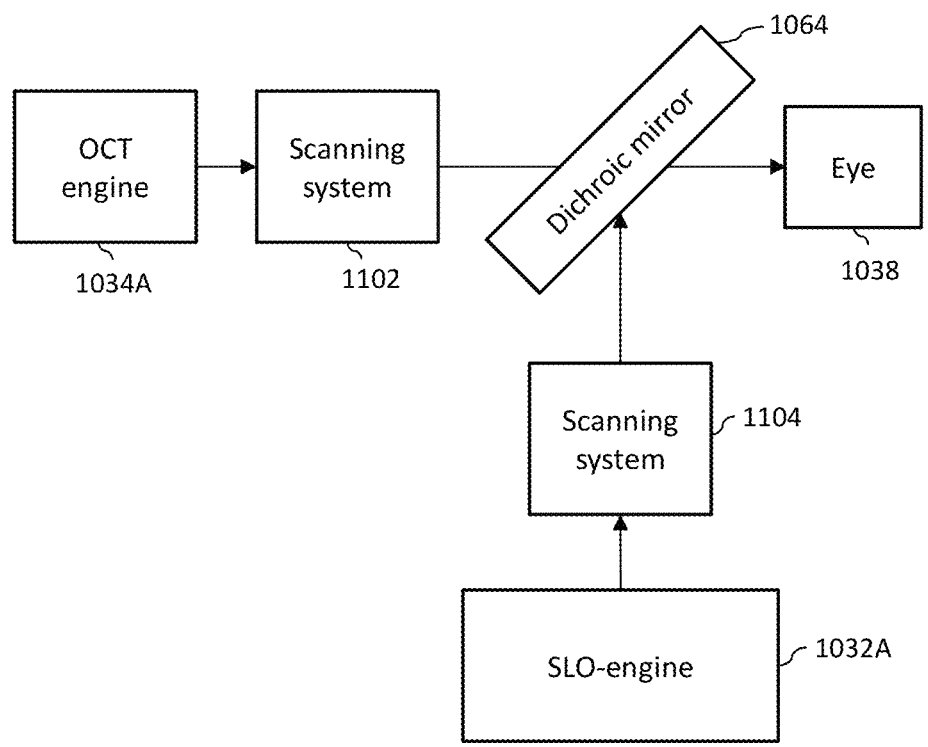
FIG. 17 is a schematic illustration of the optical system of the ophthalmic device of a first variant of the second embodiment.

FIG. 17 is a schematic illustration of the optical system of the ophthalmic device of a first variant of the embodiment. As illustrated in FIG. 17, a two-dimensional scanning optical system 1104 for SLO is disposed on one light incidence side (the SLO engine 1032A side) of the dichroic mirror 1064, and a two-dimensional scanning optical system 1102 for OCT is disposed at another light incidence side (the OCT engine 1034A side) of the dichroic mirror 1064.

Figure 18:
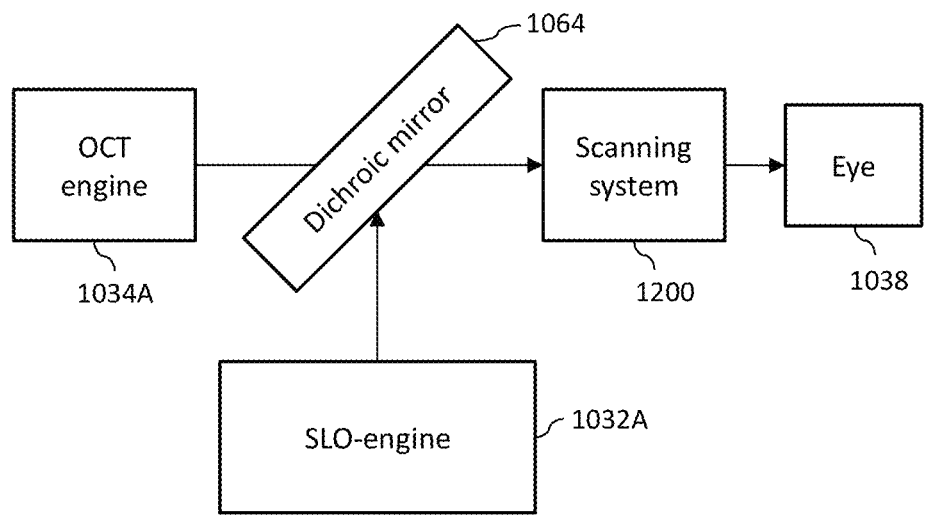
FIG. 18 is a schematic illustration of the optical system of the ophthalmic device of a second variant of the second embodiment.

FIG. 18 is a schematic illustration of the optical system of the ophthalmic device of a second variant of the embodiment. As illustrated in FIG. 18, a shared two-dimensional scanning optical system 1200, employed by SLO and OCT, is disposed at the light emission side of the dichroic mirror 1064.

Furthermore, in the all of the scanning optical systems explained above, similar scanning can be performed by exchanging the X direction with the Y direction.

Although explanation has been given regarding examples in which an ellipsoid mirror is employed as an optical member that relays the scanning, another concave mirror such as a parabolic mirror may be employed, or an optical member such as a lens may be employed instead of a concave mirror. An optical member that includes plural focal points may be employed as the optical member that relays the scanning. In such cases, the positional relationship between the optical member, the scanning optical system, and the subject's eye may adopt the following aspects.

In a first aspect, the subject's eye is disposed at one focal point position f1, and a shared two-dimensional scanning optical system, employed by SLO and OCT, is disposed at another one focal point position f2.

In a second aspect, the subject's eye is disposed at one focal point position f1, a two-dimensional scanning optical system employed by SLO is disposed at another one focal point position f2, and a two-dimensional scanning optical system employed by OCT is disposed at yet another one focal point position f3.

In a third aspect, the subject's eye is disposed at one focal point position f1, a shared one-dimensional scanning optical system employed by both SLO and OCT and that scans light in a first direction is disposed at another one focal point position f2, a one-dimensional scanning optical system that scans light in a second direction intersecting the first direction (for example, an orthogonal direction) employed by SLO is disposed at yet another one focal point position f3, and a one-dimensional scanning optical system that scans light in a second direction employed in OCT is disposed at an optically equivalent position to the another one focal point position f3.

Note that in each of the aspects above, the subject's eye and a scanning optical system may be disposed at a position optically equivalent to a focal point position instead of a focal point position.

In the exemplary embodiments explained above, a micro-electrochemical system (MEMS) mirror, a rotating mirror, a prism, a resonating mirror, or the like may be employed instead of the polygon mirror 44.

In the exemplary embodiments explained above, a MEMS mirror, a rotating mirror, a prism, a polygonal scanner, or a resonating mirror may be employed instead of the V-galvanometer mirror 60 and the H-galvanometer mirror 68.

Although examples have been given in each of the exemplary embodiments above in which a pair of concave mirrors are configured by the slit mirror 66 and the ellipsoid mirror 70, the present invention is not limited thereto. For example, a tilted spherical mirror, a non-spherical mirror, a pair of parabola mirrors, a pair of parabolic mirrors, a lens system, or an optical system employing an appropriate combination of these may be employed instead of the slit mirror 66.

Furthermore, the fixation target light control processing explained in each of the exemplary embodiments above are merely examples. It therefore goes without saying that unnecessary steps may be omitted, new steps may be added, and the processing sequence may be rearranged. Moreover, each item of OCT imaging processing may be implemented by hardware configuration alone, such as an FPGA, an ASIC, or the like, or may be implemented by a combination of a computer employing software configuration and hardware configuration.

Methods according to embodiments described above are summarised in the following numbered clauses E1 to E20:

E1. A method of operating an ophthalmic device (10-1; 10-2) having an illumination module (1-1; 1-2) arranged to scan light across a region of the retina of a subject's eye (38) to illuminate said region, the method comprising processes of:
 aligning the pupil of the eye with a focal point of the illumination module (1-1; 1-2);
 following the alignment of the pupil with the focal point, monitoring a position of the pupil relative to the focal point and maintaining the alignment of the pupil with the focal point based on the monitored position;
 performing, while the alignment of the pupil with the focal point is being maintained based on the monitored position, processes of:
  aligning a scan location of the illumination module (1-1; 1-2) on the retina to a target scan location; and
  maintaining the scan location at the target scan location, by:
   acquiring retinal feature information from a monitored portion of the retina;
   processing the acquired retinal feature information to generate scan location correction information; and
   maintaining the scan location at the target scan location using the generated scan location correction information; and
 performing a scan at the target scan location to illuminate a region of the retina at the target scan location while the scan location is being maintained at the target scan location using the generated scan location correction information.

E2. The method according to E1, wherein the pupil of the eye (38) is aligned with the focal point by monitoring the position of the pupil relative to the focal point and, based on the monitored position, adjusting the focal point of the illumination module (1-1; 1-2) so as to bring the focal point into alignment with the pupil.

E3. The method according to E1, wherein the pupil of the eye (38) is aligned with the focal point by monitoring the position of the pupil relative to the focal point and generating, based on the monitored position, at least one of:
 signals to cause the subject to move the eye so that the pupil is brought into alignment with the focal point; and
 signals to cause an operator of the ophthalmic device (10-1; 10-2) to control the focal point of the illumination module (1-1; 1-2) so as to bring the focal point into alignment with the pupil.

E4. The method according to any of E1 to E3, wherein the alignment of the pupil with the focal point is maintained by monitoring the position of the pupil relative to the focal point and adjusting the focal point of the illumination module (1-1; 1-2), based on the monitored position, so as to maintain the alignment.

E5. The method according to any of E1 to E3, wherein the alignment of the pupil with the focal point is maintained by monitoring the position of the pupil relative to the focal point and generating, based on the monitored position, at least one of:
 signals to cause the subject to move the eye so as to maintain the alignment; and
 signals to cause an operator of the ophthalmic device (10-1; 10-2) to control the focal point of the illumination module (1-1; 1-2) so as to maintain the alignment.

E6. The method according to E3 or E5, wherein the signals comprise at least one of audio signals, visual signals and tactile feedback signals.

E7. The method according to any of E1 to E6, wherein the scan location of the illumination module (1-1; 1-2) on the retina is aligned to the target scan location by:
determining an offset indicator that is indicative of an offset between a designated scan location on the retina and an initial scan location of a scan performed by the illumination module; and
controlling the illumination module (1-1; 1-2), based on the determined offset indicator, to move the scan location of the illumination module (1-1; 1-2) from the initial scan location to a destination scan location that is closer to the designated scan location than is the initial scan location, the destination scan location being the target scan location.

E8. The method according to any of E1 to E6, wherein the ophthalmic device (10-1; 10-2) further comprises a target display module (6) arranged to display a target to the subject for setting the gaze direction of the subject's eye (38), and wherein the scan location of the illumination module (1-1; 1-2) on the retina is aligned to the target scan location by:
determining an offset indicator that is indicative of an offset between a designated scan location on the retina and an initial scan location of a scan performed by the illumination module (1-1; 1-2); and
controlling the target display module (6), based on the determined offset indicator, to display the target so as to set the gaze of the subject's eye (38) in a gaze direction which brings the scan location of the illumination module (1-1; 1-2) into alignment with the target scan location.

E9. The method according to any of E1 to E8, wherein the scan location is maintained at the target scan location by:
acquiring, as the retinal feature information, images of the monitored portion of the retina while the scan is being performed by the illumination module (1-1; 1-2);
generating, as the scan location correction information, indications of respective offsets between a designated scan location and scan locations of the acquired images on the retina; and
controlling the illumination module (1-1; 1-2), based on the scan location correction information, to maintain the scan location at the target scan location.

E10. The method according to any of E1 to E8, further comprising a target display module (6) arranged to display a target to the subject for setting the gaze direction of the subject's eye (38), wherein the scan location is maintained at the target scan location by:
acquiring, as the retinal feature information, images of the monitored portion of the retina while the scan is being performed by the illumination module (1-1; 1-2);
generating, as the scan location correction information, indications of respective offsets between a designated scan location and scan locations of the acquired images on the retina; and
controlling the target display module (6), based on the scan location correction information, to vary a characteristic of the displayed target so as to maintain the gaze direction of the subject's eye (38) and keep the scan location at the target scan location.

E11. The method according to any of E1 to E10, further comprising displaying a target to the subject for setting the gaze direction of the subject's eye.

E12. The method according to E11, wherein a target for setting the gaze direction of the subject's eye along a central gaze direction is displayed to the subject.

E13. The method according to E12, comprising, while the target is displayed to set the gaze direction of the subject's eye along the central gaze direction, the processes of:
aligning the pupil of the eye with the focal point of the illumination module (1-1; 1-2); and
following the alignment of the pupil with the focal point, monitoring the position of the pupil relative to the focal point and maintaining the alignment of the pupil with the focal point based on the monitored position.

E14. The method according to E12 or E13, comprising performing, while the alignment of the pupil with the focal point is being maintained based on the monitored position and while the target is displayed to set the gaze direction of the subject's eye (38) along the central gaze direction, the processes of:
setting the scan location of the illumination module (1-1; 1-2) on the retina to the target scan location; and
following the aligning of the scan location, performing the scan at the target scan location to illuminate the region of the retina at the target scan location and, while the scan is being performed, maintaining the scan location at the target scan location.

E15. The method according to any of E1 to E6, wherein the ophthalmic device (10-2) further comprises an imaging module (7) arranged to scan light across a second region of the retina via the focal point and receive light reflected from the second region when the eye (38) is disposed at the focal point, and the method comprises, while the alignment of the pupil with the focal point is being maintained based on the monitored position:
setting the scan location of the illumination module (1-1; 1-2) on the retina to the target scan location by:
determining an offset indicator that is indicative of an offset between a designated scan location of the imaging module (7) on the retina and an initial scan location of a scan performed by the imaging module (7); and
controlling the imaging module (7), based on the determined offset indicator, to move the scan location of the imaging module (7) from the initial scan location to a destination scan location that is closer to the designated scan location than is the initial scan location, the target scan location of the illumination module (7) being the scan location of the illumination module (1-1; 1-2) while the scan location of the imaging module (7) is the destination scan location, wherein the scan location of the illumination module (1-1; 1-2) has a predetermined positional relationship to the scan location of the imaging module (7) during concurrent operation of the illumination module (1-1; 1-2) and the imaging module (7).

E16. The method according to E15, comprising, following the alignment of the scan location of the illumination module (1-1; 1-2) to the target scan location, performing the scan at the target scan location to illuminate the region of the retina at the target scan location and, while the scan is being performed, processes of:
acquiring from the imaging module (7), as the retinal feature information, a sequence of images of the retina at the destination scan location;
processing the sequence of images acquired by the imaging module (7) to generate the scan location correction information; and maintaining the scan location of the imaging module (7) at the destination scan location using the generated scan location correction information.

E17. The method according to E16, wherein the scan location of the imaging module (7) is maintained at the destination scan location by:
processing the sequence of images to generate, as the scan location correction information, retinal position tracking information that is indicative of a movement of the retina during the acquisition of the sequence images, the sequence of images being processed by:
(i) receiving at least one image of the retina;
(ii) calculating a cross-correlation between a reference image and an image based on the at least one received image to acquire an offset between the image and the reference image; and
repeating processes (i) and (ii) to acquire, as the retinal position tracking information, respective offsets for the images in the sequence; and
maintaining the scan location of the imaging module (7) using the acquired retinal tracking information.

E18. The method according to any of E15 to E17, further comprising displaying a target to the subject for setting the gaze direction of the subject's eye (38) along a central gaze direction during at least some of the processes.

E19. The method according to any of E15 to E18, wherein the imaging module (7) is arranged to acquire a wide-field image of the retina by rotating the direction of a light beam emitted thereby through an angle of at least θ about the focal point, wherein θ is one of 30 degrees, 60 degrees, and 100 degrees, and by receiving light reflected from the retina.

E20. The method according to any of E15 to E19, wherein the imaging module (7) comprises a scanning laser ophthalmoscope, and the illumination module (1-2) is further arranged to receive light reflected from the region of the retina so as to acquire an image of the region, the illumination module (1-2) comprising one of an optical coherence tomography imaging device, a high-density scanning laser ophthalmoscope, and a high-density confocal scanning laser ophthalmoscope.

Although description has been given above of exemplary embodiments of the present invention with reference to the drawings, the specific configuration of the exemplary embodiments are not limited thereto, and encompass designs and the like within a range not departing from the spirit and scope of the present invention.

All publications, patent applications and technical standards mentioned in the present specification are incorporated by reference in the present specification to the same extent as if each individual publication, patent application, or technical standard was specifically and individually indicated to be incorporated by reference.

The invention claimed is:

1. A method of operating an ophthalmic device having an illumination module arranged to scan light across a region of the retina of a subject's eye to illuminate said region, the method comprising processes of:
aligning the pupil of the eye with a focal point of the illumination module;
following the alignment of the pupil with the focal point, monitoring a position of the pupil relative to the focal point and maintaining the alignment of the pupil with the focal point based on the monitored position;
performing, while the alignment of the pupil with the focal point is being maintained based on the monitored position, processes of:
aligning a scan location of the illumination module on the retina to a target scan location; and
maintaining the scan location at the target scan location, by:
acquiring retinal feature information from a monitored portion of the retina;
processing the acquired retinal feature information to generate scan location correction information, wherein the generated scan location correction information is based on the acquired retinal feature information obtained from the monitored portion of the retina; and
maintaining the scan location at the target scan location using the generated scan location correction information; and
performing a scan at the target scan location to illuminate a region of the retina at the target scan location while the scan location is being maintained at the target scan location using the generated scan location correction information.

2. The method according to claim 1, wherein the pupil of the eye is aligned with the focal point by monitoring the position of the pupil relative to the focal point and, based on the monitored position, adjusting the focal point of the illumination module so as to bring the focal point into alignment with the pupil.

3. The method according to claim 1, wherein the pupil of the eye is aligned with the focal point by monitoring the position of the pupil relative to the focal point and generating, based on the monitored position, at least one of:
signals to cause the subject to move the eye so that the pupil is brought into alignment with the focal point; and
signals to cause an operator of the ophthalmic device to control the focal point of the illumination module so as to bring the focal point into alignment with the pupil.

4. The method according to claim 1, wherein the alignment of the pupil with the focal point is maintained by monitoring the position of the pupil relative to the focal point and adjusting the focal point of the illumination module, based on the monitored position, so as to maintain the alignment.

5. The method according to claim 1, wherein the alignment of the pupil with the focal point is maintained by monitoring the position of the pupil relative to the focal point and generating, based on the monitored position, at least one of:
signals to cause the subject to move the eye so as to maintain the alignment; and
signals to cause an operator of the ophthalmic device to control the focal point of the illumination module so as to maintain the alignment.

6. An ophthalmic device comprising:
an illumination module arranged to scan light across a region of the retina of a subject's eye to illuminate said region when the pupil of the eye is disposed at a focal point of the illumination module, the illumination module comprising:
a reflecting face arranged to reflect light emitted by an emission section and to scan the light in a specific direction by changing orientation; and
a concave mirror face arranged to reflect the light that has been reflected by the reflecting face onto the retina of the subject's eye when the subject's eye is placed at a focal point of the concave mirror face during use of the ophthalmic device;
a pupil alignment module arranged to align the pupil of the eye with the focal point;

a pupil alignment maintenance module arranged to, following the alignment of the pupil with the focal point by the pupil alignment module, monitor a position of the pupil relative to the focal point and maintain the alignment of the pupil with the focal point based on the monitored position;
a retina scan location alignment module arranged to align a scan location of the illumination module on the retina to a target scan location while the alignment of the pupil with the focal point is being maintained by the pupil alignment maintenance module, wherein the illumination module is arranged to perform a scan at the target scan location to illuminate a region of the retina at the target scan location; and
a retina scan location maintenance module arranged to maintain the scan location at the target scan location by performing, while the alignment of the pupil with the focal point is being maintained by the pupil alignment maintenance module, processes of:
  acquiring retinal feature information from a monitored portion of the retina;
  processing the acquired retinal feature information to generate scan location correction information, wherein the generated scan location correction information is based on the acquired retinal feature information obtained from the monitored portion of the retina; and
  maintaining the scan location at the target scan location using the generated scan location correction information.

7. The ophthalmic device according to claim 6, wherein the pupil alignment module is arranged to align the pupil of the eye with the focal point by monitoring the position of the pupil relative to the focal point and:
  based on the monitored position, adjusting the focal point of the illumination module so as to bring the focal point into alignment with the pupil; or
  generating, based on the monitored position, at least one of:
  signals to cause the subject to move the eye so that the pupil is brought into alignment with the focal point and
  signals to cause an operator of the ophthalmic device to control the focal point of the illumination module so as to bring the focal point into alignment with the pupil.

8. The ophthalmic device according to claim 6, wherein the pupil alignment maintenance module is arranged to maintain the alignment of the pupil with the focal point by monitoring the position of the pupil relative to the focal point and:
  adjusting the focal point of the illumination module, based on the monitored position, so as to maintain the alignment, or
  generating, based on the monitored position, at least one of:
  signals to cause the subject to move the eye so as to maintain the alignment; and
  signals to cause an operator of the ophthalmic device to control the focal point of the illumination module so as to maintain the alignment.

9. The ophthalmic device according to claim 7, wherein the pupil alignment maintenance module is arranged to maintain the alignment of the pupil with the focal point by monitoring the position of the pupil relative to the focal point and generating, based on the monitored position, the at least one of the signals to cause the subject to move the eye so as to maintain the alignment, and the signals to cause the operator of the ophthalmic device to control the focal point of the illumination module so as to maintain the alignment, and wherein the signals comprise at least one of audio signals, visual signals and tactile feedback signals.

10. The ophthalmic device according to claim 6, wherein the retina scan location alignment module is arranged to align the scan location of the illumination module on the retina to the target scan location by:
  determining an offset indicator that is indicative of an offset between a designated scan location on the retina and an initial scan location of a scan performed by the illumination module; and
  controlling the illumination module, based on the determined offset indicator, to move the scan location of the illumination module from the initial scan location to a destination scan location that is closer to the designated scan location than is the initial scan location, the destination scan location being the target scan location.

11. The ophthalmic device according to claim 6, wherein the ophthalmic device further comprises a target display module arranged to display a target to the subject for setting the gaze direction of the subject's eye, and wherein the retina scan location alignment module is arranged to align the scan location of the illumination module on the retina to the target scan location by:
  determining an offset indicator that is indicative of an offset between a designated scan location on the retina and an initial scan location of a scan performed by the illumination module; and
  controlling the target display module, based on the determined offset indicator, to display the target so as to set the gaze of the subject's eye in a gaze direction which brings the scan location of the illumination module into alignment with the target scan location.

12. The ophthalmic device according to claim 6, wherein the retina scan location maintenance module is arranged to maintain the scan location at the target scan location by:
  acquiring, as the retinal feature information, images of the monitored portion of the retina while the scan is being performed by the illumination module;
  generating, as the scan location correction information, indications of respective offsets between a designated scan location and scan locations of the acquired images on the retina; and
  controlling the illumination module, based on the scan location correction information, to maintain the scan location at the target scan location.

13. The ophthalmic device according to claim 6, further comprising:
  a target display module arranged to display a target to the subject for setting the gaze direction of the subject's eye,
  wherein the retina scan location maintenance module is arranged to maintain the scan location at the target scan location by:
  acquiring, as the retinal feature information, images of the monitored portion of the retina while the scan is being performed by the illumination module;
  generating, as the scan location correction information, indications of respective offsets between a designated scan location and scan locations of the acquired images on the retina; and
  controlling the target display module, based on the scan location correction information, to vary a characteristic of the displayed target so as to maintain the gaze direction of the subject's eye and keep the scan location at the target scan location.

14. The ophthalmic device according to claim 6, further comprising a target display module arranged to display a target to the subject for setting the gaze direction of the subject's eye.

15. The ophthalmic device according to claim 14, wherein the target display module is arranged to display a target to the subject for setting the gaze direction of the subject's eye along a central gaze direction, and wherein:
the pupil alignment module is arranged to align the pupil of the eye with the focal point while the target display module is displaying the target to set the gaze direction of the subject's eye along the central gaze direction; and
the pupil alignment maintenance module is arranged to, following the alignment of the pupil with the focal point by the pupil alignment module and while the target display module is displaying the target to set the gaze direction of the subject's eye along the central gaze direction, monitor the position of the pupil relative to the focal point and maintain the alignment of the pupil with the focal point based on the monitored position.

16. The ophthalmic device according to claim 15, wherein:
the retina scan location alignment module is arranged to align the scan location of the illumination module on the retina to the target scan location while the alignment of the pupil with the focal point is being maintained by the pupil alignment maintenance module and while the target display module is displaying the target to set the gaze direction of the subject's eye along the central gaze direction; and
the retina scan location maintenance module is arranged to maintain the scan location at the target scan location while the scan is being performed at the target scan location by the illumination module and while the target display module is displaying the target to set the gaze direction of the subject's eye along the central gaze direction.

17. The ophthalmic device according to claim 6, further comprising:
an imaging module arranged to scan light across a second region of the retina via the focal point and receive light reflected from the second region when the eye is disposed at the focal point,
wherein the retinal scan location alignment module is arranged to align the scan location of the illumination module on the retina to the target scan location, while the alignment of the pupil with the focal point is being maintained by the pupil alignment maintenance module, by:
determining an offset indicator that is indicative of an offset between a designated scan location of the imaging module on the retina and an initial scan location of a scan performed by the imaging module; and
controlling the imaging module, based on the determined offset indicator, to move the scan location of the imaging module from the initial scan location to a destination scan location that is closer to the designated scan location than is the initial scan location, the target scan location of the illumination module being the scan location of the illumination module while the scan location of the imaging module is the destination scan location, wherein the scan location of the illumination module has a predetermined positional relationship to the scan location of the imaging module during concurrent operation of the illumination module and the imaging module.

18. The ophthalmic device according to claim 17, wherein the retina scan location maintenance module is arranged to maintain the scan location of the illumination module at the target scan location by performing, while the alignment of the pupil with the focal point is being maintained by the pupil alignment maintenance module and during the performance of the scan at the target scan location by the illumination module, processes of:
acquiring from the imaging module, as the retinal feature information, a sequence of images of the retina at the destination scan location;
processing the sequence of images acquired by the imaging module to generate the scan location correction information; and
maintaining the scan location of the imaging module at the destination scan location using the generated scan location correction information.

19. The ophthalmic device according to claim 18, wherein the retina scan location maintenance module is arranged to maintain the scan location of the illumination module at the target scan location by:
processing the acquired sequence of images to generate, as the scan location correction information, retinal position tracking information that is indicative of a movement of the retina during the acquisition of the sequence images, the sequence of images being processed by:
(i) receiving at least one image of the retina;
(ii) calculating a cross-correlation between a reference image and an image based on the at least one received image to acquire an offset between the image and the reference image; and
repeating processes (i) and (ii) to acquire, as the retinal position tracking information, respective offsets for the images in the sequence; and
maintaining the scan location of the imaging module using the acquired retinal tracking information.

20. The ophthalmic device according to claim 17, wherein the imaging module comprises a scanning laser ophthalmoscope, and the illumination module is further arranged to receive light reflected from the region of the retina so as to acquire an image of the region, the illumination module comprising one of an optical coherence tomography imaging device, a high-density scanning laser ophthalmoscope, and a high-density confocal scanning laser ophthalmoscope.

* * * * *